(12) United States Patent
Bishop et al.

(10) Patent No.: US 12,274,512 B2
(45) Date of Patent: Apr. 15, 2025

(54) INDICATOR SYSTEM

(71) Applicant: CMR SURGICAL LIMITED, Cambridge (GB)

(72) Inventors: Steven Bishop, Walden (GB); Ricardo Michael Henderson Da Silva, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 705 days.

(21) Appl. No.: 17/282,676

(22) PCT Filed: Oct. 3, 2019

(86) PCT No.: PCT/GB2019/052795
§ 371 (c)(1),
(2) Date: Apr. 2, 2021

(87) PCT Pub. No.: WO2020/070504
PCT Pub. Date: Apr. 9, 2020

(65) Prior Publication Data
US 2021/0345893 A1 Nov. 11, 2021

(30) Foreign Application Priority Data
Oct. 3, 2018 (GB) .................................. 1816168

(51) Int. Cl.
*A61B 34/20* (2016.01)
*A61B 1/00* (2006.01)
(Continued)

(52) U.S. Cl.
CPC ........ *A61B 34/20* (2016.02); *A61B 1/000094* (2022.02); *A61B 5/0205* (2013.01);
(Continued)

(58) Field of Classification Search
CPC ......... A61B 34/25; A61B 34/30; A61B 90/36; A61B 90/50; A61B 5/0205; A61B 5/7405;
(Continued)

(56) References Cited

U.S. PATENT DOCUMENTS 5,123,056 A 6/1992 Wilson
5,528,289 A 6/1996 Cortjens et al.
(Continued)

FOREIGN PATENT DOCUMENTS

CA 3067299 A1 3/2013
CA 2902771 C 8/2018
(Continued)

OTHER PUBLICATIONS

Australian Examination Report No. 1 from corresponding Australian Application No. 2019352792 dated Mar. 10, 2022.
(Continued)

*Primary Examiner* — John J Lee
(74) *Attorney, Agent, or Firm* — Lando & Anastasi, LLP

(57) ABSTRACT

An indicator system for a surgical robotic system for indicating a state of at least a portion of patient anatomy, the surgical robotic system comprising a robot having a base and an arm extending from the base, the arm holding an endoscope at an end of the arm distal from the base, the endoscope being configured for insertion into a body cavity of the patient for observing a surgical site internal to a body of the patient, the indicator system comprising: a receiver configured to receive video data of at least a portion of patient anatomy at the surgical site from the endoscope; and a processor configured to: detect a spatio-temporal change in a pixel region of the received video data; identify, in response to the detected spatio-temporal change, a parameter of the patient anatomy; generate a health indicator
(Continued)

indicative of the identified parameter or indicative of a profile of the identified parameter; and output the generated health indicator.

20 Claims, 13 Drawing Sheets

(51) Int. Cl.
- A61B 5/00 (2006.01)
- A61B 5/0205 (2006.01)
- A61B 34/00 (2016.01)
- A61B 34/30 (2016.01)
- A61B 34/35 (2016.01)
- A61B 90/00 (2016.01)
- A61B 90/50 (2016.01)
- A61B 34/10 (2016.01)

(52) U.S. Cl.
CPC ............ *A61B 5/7405* (2013.01); *A61B 5/742* (2013.01); *A61B 5/7455* (2013.01); *A61B 34/25* (2016.02); *A61B 34/30* (2016.02); *A61B 34/35* (2016.02); *A61B 34/74* (2016.02); *A61B 90/36* (2016.02); *A61B 90/361* (2016.02); *A61B 90/50* (2016.02); *A61B 2034/102* (2016.02); *A61B 2034/105* (2016.02); *A61B 2034/107* (2016.02); *A61B 2034/2055* (2016.02); *A61B 2034/2065* (2016.02); *A61B 2034/2074* (2016.02); *A61B 2034/301* (2016.02); *A61B 2034/302* (2016.02); *A61B 2090/365* (2016.02)

(58) Field of Classification Search
CPC . A61B 5/742; A61B 5/7455; A61B 2034/301; A61B 2034/302; A61B 2090/365
See application file for complete search history.

(56) References Cited

U.S. PATENT DOCUMENTS

| | | | |
|---|---|---|---|
| 9,547,940 | B1 | 1/2017 | Sun et al. |
| 10,058,396 | B1 | 8/2018 | Genova et al. |
| 10,939,970 | B2* | 3/2021 | Laakso ................ A61B 34/37 |
| 2002/0016540 | A1 | 2/2002 | Mikus et al. |
| 2005/0065435 | A1 | 3/2005 | Rauch et al. |
| 2009/0232374 | A1 | 9/2009 | Simon |
| 2009/0326556 | A1* | 12/2009 | Diolaiti .............. A61B 1/00154 606/130 |
| 2010/0317965 | A1 | 12/2010 | Itkowitz et al. |
| 2011/0282140 | A1 | 11/2011 | Itkowitz et al. |
| 2012/0029504 | A1 | 2/2012 | Afonso et al. |
| 2012/0053408 | A1 | 3/2012 | Miyamoto |
| 2012/0092348 | A1 | 4/2012 | McCutchen |
| 2013/0038707 | A1 | 2/2013 | Cunningham et al. |
| 2014/0005484 | A1 | 1/2014 | Charles |
| 2014/0275760 | A1 | 9/2014 | Lee et al. |
| 2016/0225192 | A1 | 8/2016 | Jones et al. |
| 2017/0105803 | A1 | 4/2017 | Wong et al. |
| 2017/0161893 | A1* | 6/2017 | Carnes .................. G06T 19/006 |
| 2017/0172696 | A1 | 6/2017 | Saget et al. |
| 2018/0101992 | A1 | 4/2018 | Akselrod et al. |
| 2018/0168741 | A1* | 6/2018 | Swayze .................. A61B 90/37 |
| 2018/0253861 | A1 | 9/2018 | Moteki et al. |
| 2021/0369354 | A1 | 12/2021 | Hares et al. |

FOREIGN PATENT DOCUMENTS

| | | |
|---|---|---|
| CA | 3066476 C | 11/2022 |
| CN | 102170835 A | 8/2011 |
| CN | 104428818 A | 3/2015 |
| CN | 106535805 A | 3/2017 |
| CN | 106663318 A | 5/2017 |
| CN | 107610109 A | 1/2018 |
| CN | 107847274 A | 3/2018 |
| CN | 107847289 A | 3/2018 |
| CN | 108472095 A | 8/2018 |
| CN | 108537785 A | 9/2018 |
| CN | 109035414 A | 12/2018 |
| GB | 2558284 A | 7/2018 |
| JP | 201017555 A | 1/2010 |
| JP | 2010005326 A | 1/2010 |
| JP | 2012529970 A | 11/2012 |
| JP | 2014504896 A | 2/2014 |
| JP | 2015521913 A | 8/2015 |
| JP | 2016536098 A | 11/2016 |
| JP | 2016538014 A | 12/2016 |
| JP | 2017006337 A | 1/2017 |
| JP | 2017529914 A | 10/2017 |
| WO | 2006057663 A2 | 6/2006 |
| WO | 2012067682 A1 | 5/2012 |
| WO | 2015187866 A1 | 12/2015 |
| WO | 2016014384 A2 | 1/2016 |
| WO | 2017057414 A1 | 4/2017 |
| WO | 2017057574 A1 | 4/2017 |
| WO | 2017058710 A1 | 4/2017 |
| WO | 2017147596 A1 | 8/2017 |

OTHER PUBLICATIONS

Indian Examination Report from corresponding Indian Application No. 202127019545 dated Feb. 11, 2022.
Indian Examination Report from corresponding Indian Application No. 202127019908 dated Jul. 27, 2022.
Indian First Examination Report from corresponding Indian Application No. 202127019544 dated Feb. 11, 2022.
International Preliminary Report on Patentability and Written Opinion of the International Searching Authority from corresponding PCT/GB2019/052793 dated Mar. 23, 2021.
International Preliminary Report on Patentability and Written Opinion of the International Searching Authority from corresponding PCT/GB2019/052795 dated Mar. 23, 2021.
Notification of Transmittal of the International Search Report and the Written Opinion of the International Searching Authority from corresponding PCT/GB2019/052791 dated Dec. 16, 2019.
Notification of Transmittal of the International Search Report and the Written Opinion of the International Searching Authority from corresponding PCT/GB2019/052793 dated Dec. 16, 2019.
United Kingdom Combined Search and Examination Report from corresponding United Kingdom Application No. GB2209898.2 dated Oct. 4, 2022.
United Kingdom Examination Report from corresponding United Kingdom Application No. GB1816169.5 dated May 4, 2022.
United Kingdom Search Report from corresponding United Kingdom Application No. GB1816169.5 dated Oct. 29, 2019.
Japanese Notification of Reasons for Refusal from corresponding Japanese Application No. 2021-518643 dated Sep. 5, 2023.
Japanese Notification of Reasons for Refusal from corresponding Japanese Application No. 2021-518643 dated Mar. 7, 2023.
Japanese Notification of Reasons for Refusal from corresponding Japanese Application No. 2021-518657 dated May 10, 2022.
United Kingdom Combined Search and Examination Report from corresponding United Kingdom Application No. GB2301588.6 dated Feb. 10, 2023.
Notification of Transmittal of the International Search Report and the Written Opinion of the International Searching Authority from corresponding PCT/GB2019/052795 dated Dec. 18, 2019.
United Kingdom Search Report from corresponding United Kingdom Application No. GB1816168.7 dated Mar. 29, 2019.
Chinese First Office Action from corresponding Chinese Application No. 201980065507.6 dated Jan. 12, 2024.
Chinese Office Action from corresponding Chinese Application No. 201980065300.9 dated Dec. 22, 2023.
Chinese Office Action from corresponding Chinese Application No. 201980065492.3 dated Jan. 2, 2024.
European Examination Report from corresponding European Application No. 19787373.0 dated Aug. 26, 2024.

(56) References Cited

OTHER PUBLICATIONS

Chinese Notice of Grant of Patent Right to Invention from corresponding Chinese Application No. 201980065492.3 dated Oct. 25, 2024.
Chinese Summary of the Rejection Decision from corresponding Chinese Application No. 201980065300.9 dated Nov. 5, 2024.
European Examination Report from corresponding European Application No. 19787371.4 dated Aug. 1, 2024.

* cited by examiner

INDICATOR SYSTEM

CROSS-REFERENCE TO RELATED APPLICATIONS

This application is a U.S. National Phase Application under 35 U.S.C. § 371 of International Application No. PCT/GB2019/052795, filed Oct. 3, 2019, which claims priority to United Kingdom Application No. 1816168.7, filed Oct. 3, 2018. Each application referenced above is hereby incorporated by reference in its entirety for all purposes.

BACKGROUND

It is known to use robots for assisting and performing surgery. FIG. 1 illustrates a typical surgical robot 100 which consists of a base 108, an arm 102, and an instrument 105. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 so as to access the surgical site. At its distal end, the instrument comprises an end effector 106 for engaging in a medical procedure.

FIG. 2 illustrates a typical surgical instrument 200 for performing robotic laparoscopic surgery. The surgical instrument comprises a base 201 by means of which the surgical instrument connects to the robot arm. A shaft 202 extends between the base 201 and an articulation 203. The articulation 203 terminates in an end effector 204. In FIG. 2, a pair of serrated jaws are illustrated as the end effector 204. The articulation 203 permits the end effector 204 to move relative to the shaft 202. It is desirable for at least two degrees of freedom to be provided to the motion of the end effector 204 by means of the articulation.

An imaging device can be located at a surgical site together with the surgical instrument. The imaging device can image the surgical site. The image of the surgical site provided by the imaging device can be displayed on a display for viewing by a surgeon carrying out the procedure. Laparoscopic (or minimally invasive) surgery, where the surgeon does not have a direct line of sight to the surgical site, can therefore be performed.

SUMMARY

According to an aspect of the present invention there is provided an indicator system for a surgical robotic system for indicating a state of at least a portion of patient anatomy, the surgical robotic system comprising a robot having a base and an arm extending from the base, the arm holding an endoscope at an end of the arm distal from the base, the endoscope being configured for insertion into a body cavity of the patient for observing a surgical site internal to a body of the patient, the indicator system comprising:
 a receiver configured to receive video data of at least a portion of patient anatomy at the surgical site from the endoscope; and
 a processor configured to:
  detect a spatio-temporal change in a pixel region of the received video data;
  identify, in response to the detected spatio-temporal change, a parameter of the patient anatomy;
  generate a health indicator indicative of the identified parameter or indicative of a profile of the identified parameter; and
  output the generated health indicator.

The processor may be configured to compare the identified parameter with a reference parameter of the patient anatomy, and to generate the health indicator in dependence on a result of the comparison. The spatio-temporal change may comprise one or more of: a positional change of at least a portion of the patient anatomy in the pixel region; an intensity change of at least a portion of the patient anatomy in the pixel region; and a change in the frequency spectrum of at least a portion of the patient anatomy in the pixel region.

The processor may be configured to identify a relative movement between the endoscope and a bulk of the patient anatomy and/or between the bulk of the patient anatomy and a remainder of the surgical site and to detect the spatio-temporal change in dependence on the identified relative movement.

The processor may be configured to amplify the spatio-temporal change and to generate the health indicator using the amplified spatio-temporal change. Where the spatio-temporal change comprises a change between a first value and a second value, the processor may be configured to amplify the spatio-temporal change by multiplying the first value with a first amplification factor and by multiplying the second value by a second amplification factor. One or both of the first amplification factor and the second amplification factor may be greater than 1. One or both of the first amplification factor and the second amplification factor may be selected in dependence on one or more of: a number of detected spatio-temporal changes in the pixel region; a surgeon preference; a procedure being carried out using the surgical robotic system or a stage of the procedure; the patient anatomy; the identified parameter; and the comparison of the identified parameter with the reference parameter.

The pixel region may comprise at least a portion of the field of view of the endoscope. The processor may be configured to select the pixel region in response to one or more of a received user selection signal and an anatomical structure identifying signal. The surgical robotic system may comprise a controller having an input device for controlling an arm of the surgical robotic system, the controller being configured to output the user selection signal in response to user input relating to the surgical site. The processor may be configured to identify, in the received video data, one or more anatomical structure and to output the anatomical structure identifying signal in response to identifying the one or more anatomical structure. The pixel region may comprise at least a portion of an anatomical structure. The spatio-temporal change may comprise a peristaltic movement of at least a portion of an anatomical structure.

The pixel region may comprise one or more of: a representation of at least a portion of a ureter, and the spatio-temporal change comprises a peristaltic movement of the ureter; and a representation of at least a portion of a bowel, and the spatio-temporal change comprises a peristaltic movement of the bowel. The spatio-temporal change may represent a measure of tissue perfusion or blood flow.

The processor may be configured to calibrate the identified parameter using a further parameter. The parameter and further parameter may relate to one or both of a patient heart rate and a patient respiratory rate. The receiver may be configured to receive further video data of an external portion of the patient and the processor may be configured to: detect a further spatio-temporal change in a pixel region of the received further video data; and identify the further parameter in response to the detected further spatio-temporal change.

The generated health indicator may comprise one or more of: a visual indicator and the processor is configured to output the generated health indicator for display on a display; an audio indicator and the processor is configured to output the generated health indicator for driving a speaker; and a haptic indicator and the processor is configured to output the generated health indicator for driving a motor for providing haptic feedback.

According to another aspect of the present invention there is provided a method of indicating a state of at least a portion of patient anatomy, the method comprising:
  receiving, from an endoscope at a surgical site internal to a body cavity of a patient, video data of at least a portion of patient anatomy at the surgical site;
  detecting a spatio-temporal change in a pixel region of the received video data;
  identifying, in response to the detected spatio-temporal change, a parameter of the patient anatomy;
  generating a health indicator indicative of the identified parameter or indicative of a profile of the identified parameter; and
  outputting the generated health indicator.

According to another aspect of the present invention there is provided an indicator system for a surgical robotic system configured to perform the method as described herein.

According to another aspect of the present invention there is provided a non-transitory computer readable storage medium having stored thereon computer readable instructions that, when executed at a computer system, cause the computer system to perform the method as described herein.

According to another aspect of the present invention there is provided a surgical robotic system for augmenting a representation of a surgical site at which a surgical procedure can be carried out, the system comprising: a display configured to display part or all of a representation of at least a portion of a surgical site; a controller comprising an input device, whereby the input device can control an indicator on the display, the controller being configured to output an augmentation signal in response to user input relating to the representation; and a processor configured to receive the augmentation signal and, in response to the received augmentation signal, to augment the representation of the surgical site.

The system may further comprise an imaging device, whereby the imaging device is configured to image the surgical site and generate an image feed of the surgical site. The representation of the surgical site may be obtained in dependence on the generated image feed. The representation of the surgical site may be a 3D representation.

The system may comprise a robot arm having a surgical instrument with an end effector, whereby the representation of the surgical site may comprise a representation of the end effector, the indicator comprising a portion of the representation of the end effector.

The augmentation signal may be indicative of a feature displayed on the display. The system may be configured to associate the augmentation with the representation of the surgical site in dependence on the indicator position. The processor may be configured to augment the representation of the surgical site in dependence on joint data associated with the robotic system. The processor may be configured to associate the augmentation with a location in the representation of the surgical site determined in dependence on the joint data.

The processor may be configured to augment the representation of the surgical site in dependence on image processing of the representation.

The system may comprise a second input device, the processor being configured to augment the representation of the surgical site in dependence on user input at the second input device. At least one of the input device and the second input device may be responsive to one or more of a voice command, a gesture and a touch interaction with the respective input device.

The processor may be configured to determine that an augmentation criterion is satisfied, and to augment the representation of the surgical site in dependence on that determination. The processor may be configured to determine that the augmentation criterion is satisfied in dependence on at least one of:
  the attachment, detachment, operation and/or change of state of a surgical instrument;
  an image recognition signal indicative of an image recognition match in the representation of the surgical site;
  an error signal indicative of an error associated with the surgical robotic system;
  a time signal; and
  a signal indicating a change of a user of the surgical robotic system.

The processor may be configured to characterise a feature associated with the augmentation in the representation of the surgical site in dependence on at least one of a user input and an image recognition signal. The system may comprise a memory coupled to the processor, the memory being configured to store at least one of the representation of the surgical site and the augmentation.

According to another aspect of the present invention there is provided a method for augmenting a representation of a surgical site at which a surgical procedure can be carried out, comprising: displaying part or all of a representation of at least a portion of a surgical site; controlling an indicator on the display; receiving user input relating to the representation and outputting an augmentation signal in response to the received user input; augmenting the representation of the surgical site in response to the augmentation signal.

The method may comprise at least one of: generating the representation of the surgical site in dependence on a stored representation of the surgical site; and generating an image feed of the surgical site and generating the representation of the surgical site in dependence on the generated image feed. The indicator may comprise a portion of an imaged end effector of the surgical robotic system, and the method may comprise controlling the indicator on the display by controlling the end effector. The method may comprise augmenting the representation of the surgical site in dependence on at least one of joint data and image processing of the representation. The method may comprise determining that an augmentation criterion is satisfied, and augmenting the representation of the surgical site in dependence on that determination. The method may comprise associating the augmentation with at least one group of augmentations. The method may comprise displaying the augmentation in dependence on the group of augmentations to which the augmentation belongs.

The method may comprise, where the representation of the surgical site comprises a plurality of augmentations, determining at least one of:
  a number of augmentations;
  a distance between the plurality of augmentations;
  an area enclosed by the plurality of augmentations; and
  a volume enclosed by the plurality of augmentations.

The method may comprise displaying, on at least one of the display and an auxiliary display, one or more of:
  a number of augmentations;
  a line connecting a plurality of augmentations;
  an area enclosed by a plurality of augmentations; and
  a volume enclosed by a plurality of augmentations.

Any one or more feature of any aspect above may be combined with any one or more feature of any other aspect above. Any apparatus feature may be written as a method feature where possible, and vice versa. These have not been written out in full here merely for the sake of brevity.

This Summary is provided to introduce a selection of concepts in a simplified form that are further described below in the Detailed Description. The mention of features in this Summary does not indicate that they are key features or essential features of the invention or of the claimed subject matter, nor is it to be taken as limiting the scope of the claimed subject matter.

BRIEF DESCRIPTION OF THE DRAWINGS

The present invention will now be described by way of example with reference to the accompanying drawings.
In the drawings.

DETAILED DESCRIPTION

Figure 1:
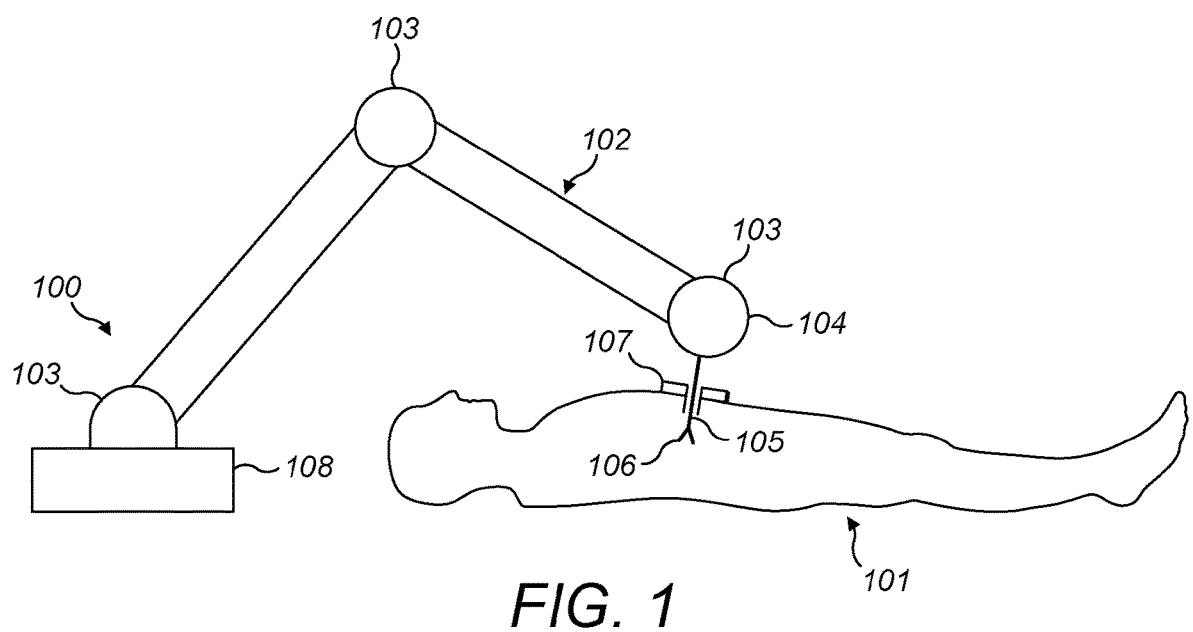
FIG. 1 illustrates a surgical robot performing a surgical procedure.

The following description describes techniques in the context of surgical robotic systems, though not all features or techniques described herein are limited to such systems, but at least some features or techniques may be applied to robotic systems more generally. At least some of the present techniques may be applied to robotic systems that operate remotely. At least some of the present techniques may be applied at sites where the user of a robotic system may become disoriented when operating the robotic system. Some examples of situations in which at least some of the present techniques may be useful include those that make use of 'snake-like' robots for exploration, investigation or repair.

Robotic systems can include manufacturing systems, such as vehicle manufacturing systems, parts handling systems, laboratory systems, and manipulators such as for hazardous materials or surgical manipulators.

The present techniques permit information such as one or more parameter relating to at least a portion of patient anatomy, for instance an anatomical structure, to be extracted from surgical video captured from an internal surgical site during a procedure such as a laparoscopic procedure. The analysis of the video to identify these extracted parameters permits enhancement of the use of the surgical robotic system in performing surgical procedures.

For example, the surgical robotic system can detect peristaltic movements of anatomical structures within the body, such as peristaltic movements of anatomical structures visible in a pixel region of video data captured by an endoscope at a surgical site internal to the body. The pixel region can comprise one or more pixels. The identification of such peristaltic movements can permit identification of the anatomical structure itself. A particular anatomical structure may have a characteristic peristaltic movement, for example a characteristic frequency and/or amplitude of movement. Thus an identified peristaltic movement can be compared to one or more known peristaltic movements which are characteristic of anatomical structures. Where the identified peristaltic movement is within a range of a known peristaltic movement, the structure undergoing the identified peristaltic movement can be identified.

Further, it is possible to identify whether the peristaltic movement of the anatomical structure is within a normal range of such movements for that structure. If the identified movement is within a normal range then it can be determined that the anatomical structure is healthy. If the identified movement is outside the normal range then it can be determined that the anatomical structure is unhealthy. What is considered to be a 'normal range' for a given structure can depend on the physiological characteristics of the patient, the procedure being performed, the stage in the procedure and so on.

The identification of peristaltic movements can aid the identification of structures from surrounding structures or from the surgical site more generally.

The techniques described herein include a system for indicating a state of at least a portion of patient anatomy such as an anatomical structure of a patient. The state of the anatomy or anatomical structure can be, or can be representative of, a state of health of the patient. Endoscope video, captured by an endoscope at an internal surgical site, can be analysed to detect spatial and/or temporal changes (referred to as spatio-temporal changes) in the video data. These changes can be representative of movement of anatomical structures and/or of blood flow through anatomical structures. The spatio-temporal changes can be used to identify one or more parameter of the anatomical structure. For example, the parameter can relate to a movement, or rate of movement, of that structure. The parameter can relate to the flow of, or rate of flow of, blood through or past that structure. The parameter can relate to a measure of tissue perfusion. A health indicator can be generated which indicates the parameter or a profile, such as a time profile, of the parameter. The health indicator can be output. The health indicator can be output so as to notify a user of the system, such as a surgeon, of the health indicator. For example, the health indicator can be a visual signal output to a display and/or an audio signal output to a speaker and/or a haptic signal output to a motor for providing haptic feedback (for example the haptic feedback can be provided via a haptic-enabled input device).

The health indicator can help the surgeon assess the state of the anatomical structure (and/or of the patient) during a surgical procedure.

Figure 3:
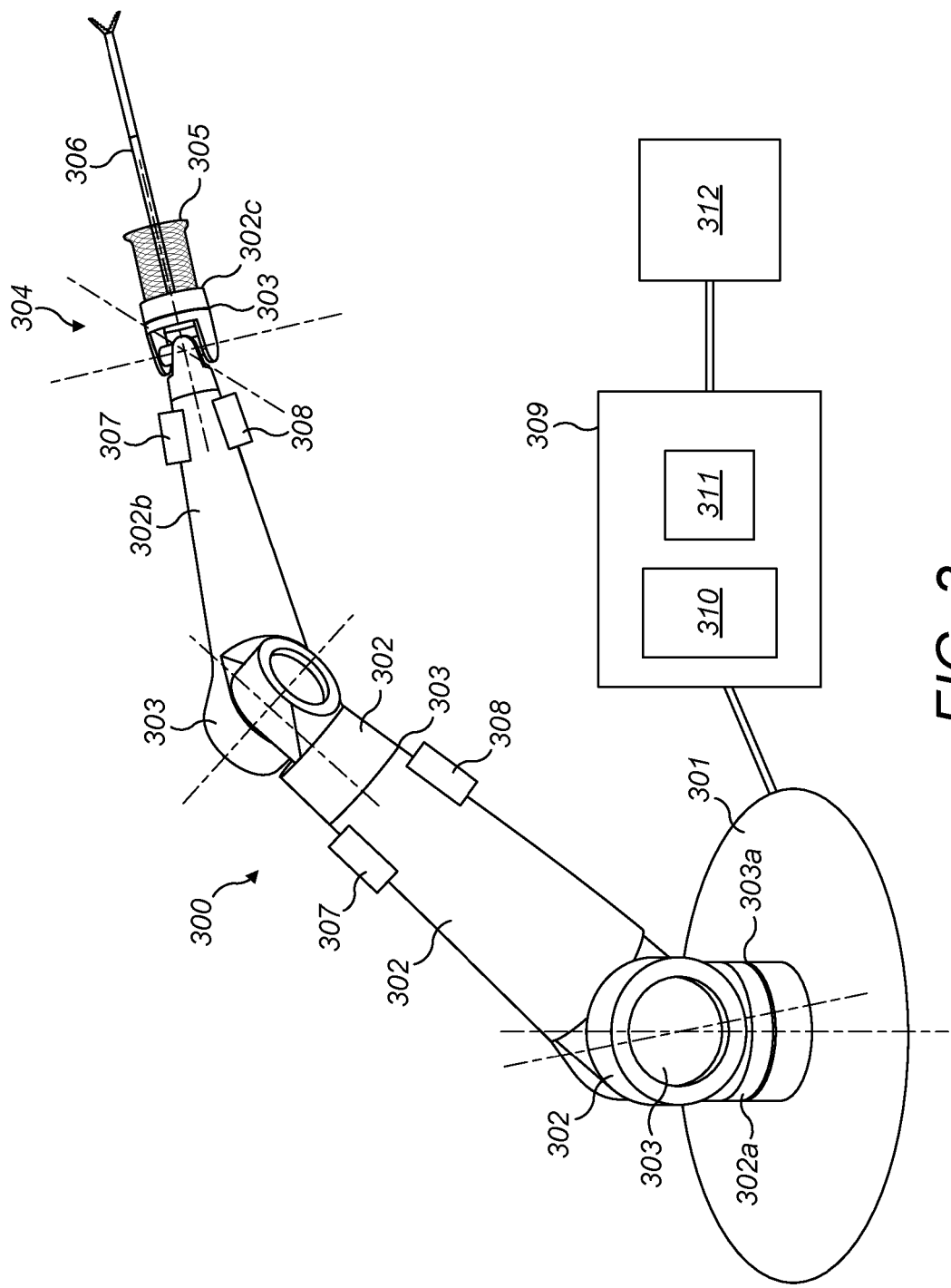
FIG. 3 illustrates a surgical robot.

FIG. 3 illustrates a surgical robot having an arm 300 which extends from a base 301. The arm comprises a number of rigid limbs 302. The limbs are coupled by revolute joints 303. The most proximal limb 302a is coupled to the base by a proximal joint 303a. It and the other limbs are coupled in series by further ones of the joints 303. Suitably, a wrist 304 is made up of four individual revolute joints. The wrist 304 couples one limb (302b) to the most distal limb (302c) of the arm. The most distal limb 302c carries an attachment 305 for a surgical instrument 306. Each joint 303 of the arm has one or more motors 307 which can be operated to cause rotational motion at the respective joint, and one or more position and/or torque sensors 308 which provide information regarding the current configuration and/or load at that joint. Suitably, the motors are arranged proximally of the joints whose motion they drive, so as to improve weight distribution. For clarity, only some of the motors and sensors are shown in FIG. 3. The arm may be generally as described in our co-pending patent application PCT/GB2014/053523.

Figure 2:
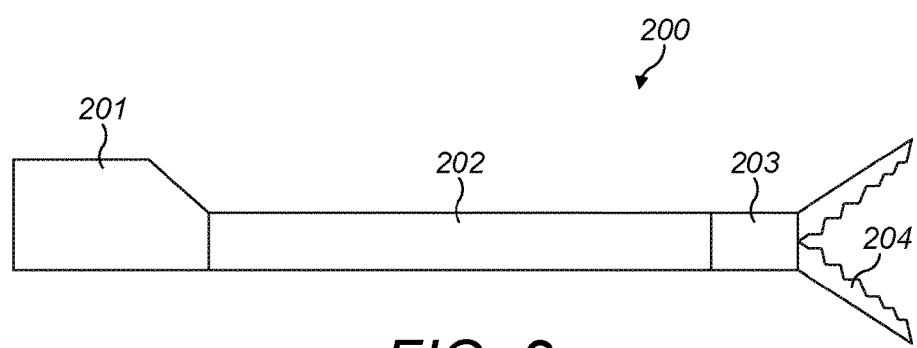
FIG. 2 illustrates a known surgical instrument.

The arm terminates in the attachment 305 for interfacing with the instrument 306. Suitably, the instrument 306 takes the form described with respect to FIG. 2. The instrument has a diameter less than 8 mm. Suitably, the instrument has a 5 mm diameter. The instrument may have a diameter which is less than 5 mm. The instrument diameter may be the diameter of the shaft. The instrument diameter may be the diameter of the profile of the articulation. Suitably, the diameter of the profile of the articulation matches or is narrower than the diameter of the shaft. The attachment 305 comprises a drive assembly for driving articulation of the instrument. Movable interface elements of the drive assembly interface mechanically engage corresponding movable interface elements of the instrument interface in order to transfer drive from the robot arm to the instrument. One instrument is exchanged for another several times during a typical operation. Thus, the instrument is attachable to and detachable from the robot arm during the operation. Features of the drive assembly interface and the instrument interface aid their alignment when brought into engagement with each other, so as to reduce the accuracy with which they need to be aligned by the user.

The instrument 306 comprises an end effector for performing an operation. The end effector may take any suitable form. For example, the end effector may be smooth jaws, serrated jaws, a gripper, a pair of shears, a needle for suturing, a camera, a laser, a knife, a stapler, a cauteriser, a suctioner. As described with respect to FIG. 2, the instrument comprises an articulation between the instrument shaft and the end effector. The articulation comprises several joints which permit the end effector to move relative to the shaft of the instrument. The joints in the articulation are actuated by driving elements, such as cables. These driving elements are secured at the other end of the instrument shaft to the interface elements of the instrument interface. Thus, the robot arm transfers drive to the end effector as follows: movement of a drive assembly interface element moves an instrument interface element which moves a driving element which moves a joint of the articulation which moves the end effector.

Controllers for the motors, torque sensors and encoders are distributed within the robot arm. The controllers are connected via a communication bus to a control unit 309. The control unit 309 comprises a processor 310 and a memory 311. The memory 311 stores in a non-transient way software that is executable by the processor to control the operation of the motors 307 to cause the arm 300 to operate in the manner described herein. In particular, the software can control the processor 310 to cause the motors (for example via distributed controllers) to drive in dependence on inputs from the sensors 308 and from a surgeon command interface 312. The control unit 309 is coupled to the motors 307 for driving them in accordance with outputs generated by execution of the software. The control unit 309 is coupled to the sensors 308 for receiving sensed input from the sensors, and to the command interface 312 for receiving input from it. The respective couplings may, for example, each be electrical or optical cables, and/or may be provided by a wireless connection. The command interface 312 comprises one or more input devices whereby a user can request motion of the end effector in a desired way. The input devices could, for example, be manually operable mechanical input devices such as control handles or joysticks, or contactless input devices such as optical gesture sensors. The software stored in the memory 311 is configured to respond to those inputs and cause the joints of the arm and instrument to move accordingly, in compliance with a pre-determined control strategy. The control strategy may include safety features which moderate the motion of the arm and instrument in response to command inputs. Thus, in summary, a surgeon at the command interface 312 can control the instrument 306 to move in such a way as to perform a desired surgical procedure. The control unit 309 and/or the command interface 312 may be remote from the arm 300.

Some surgical procedures may require several surgical robot arms, each one carrying an instrument or other implement which is used concurrently with the others at the surgical site. Such surgical robots are often used in endoscopic surgery (e.g. laparoscopic surgery), which also may be referred to as minimally invasive surgery. As is known to those of skill in the art, during an endoscopic procedure the surgeon inserts an endoscope through a small incision or natural opening in the body, such as, but not limited to, the mouth or nostrils. An endoscope is a rigid or flexible tube with a camera attached thereto that transmits real-time images to a video monitor (e.g. a display of or coupled to the system) that the surgeon uses to help guide their tools through the same incision/opening or through a different incision/opening. The endoscope allows the surgeon to view the relevant area of the body in detail without having to cut open and expose the relevant area. This technique allows the surgeon to see inside the patient's body and operate through a much smaller incision than would otherwise be required for traditional open surgery. Accordingly, in a typical robotic endoscopic surgery there is an endoscope attached to one surgical robot arm and one or more other surgical instruments, such as a pair of pincers and/or scissors, attached to one or more other surgical robot arms.

Figure 11:
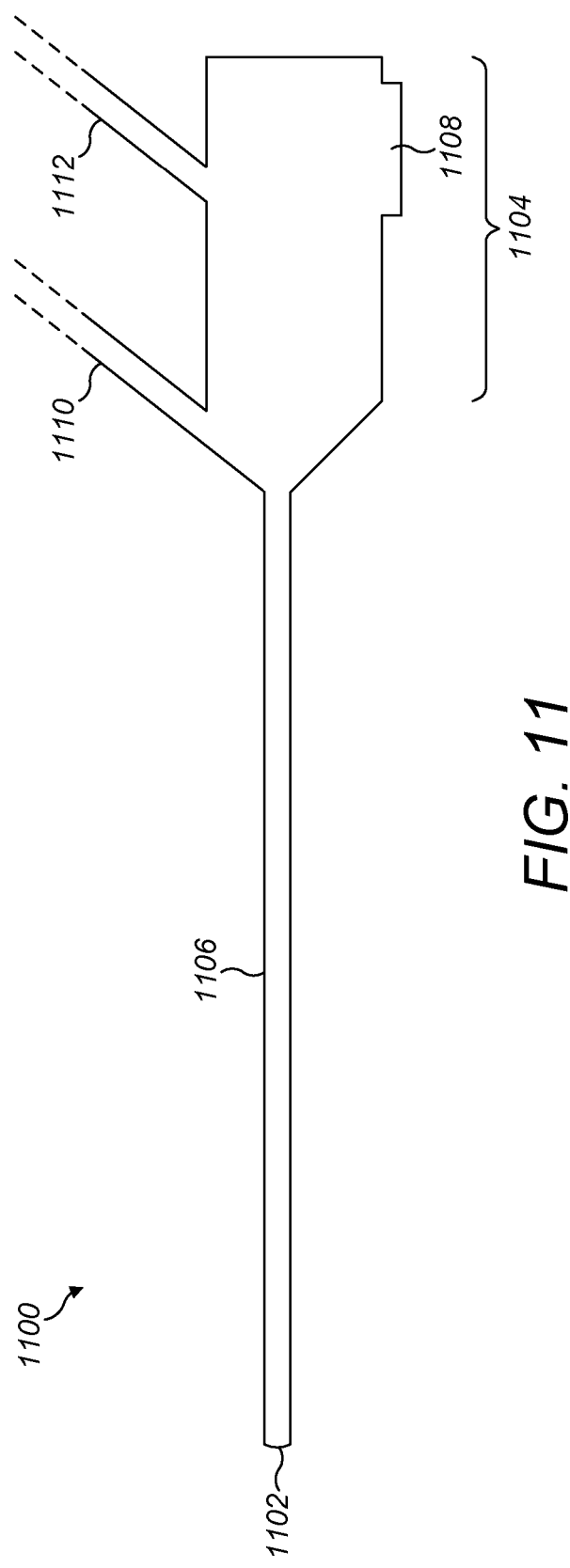
FIG. 11 illustrates an example endoscope.

FIG. 11 illustrates an example endoscope 1100 which is attachable to the end of a robot arm for use in minimally invasive surgery. The endoscope 1100 has a distal end 1102 for insertion into the surgical site of the patient, and a proximal end 1104. The distal end 1102 is connected to the proximal end 1104 by an elongate shaft 1106. The proximal end 1104 comprises an interface 1108 for engaging the end of the robot arm. The endoscope 1100 has a power source and a light source for illuminating the surgical site. The endoscope 1100 also has a data line for extracting the image data from the surgical site. These may all be attached to the proximal end 1104 of the endoscope 1100 independently and externally of the robot arm, as shown in FIG. 11. In FIG. 11, power is applied through stem 1112, image data is extracted through stem 1112, and light is applied through light stem 1110. In an alternative implementation, any one or more of the light input, power input and data output may be applied/extracted to the endoscope through the robot arm. The endoscope 1100 mounts to the end of the robot arm. The endoscope interface 1108 engages a complementary interface of the robot arm. The endoscope 1100 is attachable to and detachable from the robot arm via the robot arm and endoscope interfaces. In some cases, the endoscope 1100 is operable independently of the robot arm in its detached state. In other words, in these cases the endoscope 1100 can be operated manually by a member of the operating room staff when detached from the robot arm.

In addition to the images captured by the endoscope (which may be collectively referred to herein as the endoscope video) being used during surgery, the images captured by the endoscope may be recorded and subsequently used for a variety of purposes such as, but not limited to, learning and/or teaching surgical procedures, and assessing and/or reviewing the performance of the surgeon (by a third party or by the surgeon themselves).

Suitably an imaging device is provided. The imaging device may be provided at the surgical site. The imaging device may comprise the endoscope. The robotic system may comprise the imaging device. For example, the robotic system may comprise an arm to which the imaging device is attachable and which is configured to move the imaging device around a surgical site. The imaging device is configured to output an image signal or image feed, representative of an image of a surgical site at which the imaging device is located, and/or comprising an image of the surgical site. The image signal may comprise a video signal. Suitably, the imaging device is configured to capture video data.

Whilst the above description refers to a single screen as a display device, in some examples the robotic surgical system comprises a plurality of display devices, or screens. The screens are suitably configured to display the image as a two-dimensional image and/or as a three-dimensional image. The screens can be provided on a single user console, or two or more consoles can comprise at least one screen each. This permits additional viewing screens which can be useful for allowing people other than the console user to view the surgical site, for example for training, and/or for viewing by other people in the operating room.

Representation of the Surgical Site

A representation of a surgical site can be displayed on the display, to permit the surgeon to see the site and to enable them to perform the surgical procedure. The representation can be, or can comprise, an image feed from an imaging device such as an endoscope located at the surgical site. The representation of the surgical site can comprise a 2D or 3D representation. The 3D representation can be generated from a 2D original representation by suitable processing. In some examples, the 3D representation can comprise a 3D model, for example a 3D model of a body, or of a portion of a body. For instance, where a surgical procedure is to be carried out in an abdominal cavity, the 3D model can represent such an abdominal cavity. The 3D model may, in some examples, be derived at least in part from data such as physical data relating to a patient. For example, the data can comprise data from a scan such as an MRI scan. The 3D model may be modified or selected according to knowledge of a patient to undergo a surgical procedure, for example in dependence on knowledge of that person's physiology or pathophysiology. In some examples, the representation is based on both a captured image feed and a model such as a 3D model of the site.

The 3D model is suitably a 3D anatomical model. The model may comprise a simulation or simulated data. The model may comprise model data that has been built up from data obtained in relation to earlier procedures. The earlier procedures may be in respect of a single patient, which may be the same patient. The earlier procedures may be in respect of more than one patient. The earlier procedures may be of the same or similar type to the procedure being planned or performed.

The representation of the surgical site is likely to change during a surgical procedure. For example, the representation may change as a patient moves (for example where the orientation of a patient changes such as where a patient table is tilted) and/or as the imaging device changes its position (or location) and/or orientation relative to the surgical site. The imaging device may pan through a surgical site, and/or zoom in or out. Such changes can also change the representation of the site displayed on the display. The portion of a model displayed on the display can change, for example during a surgical procedure. The portion of the model displayed may change in dependence on a determined position of the end effector. The position of the end effector may be determined, for example, in dependence on control signals sent to the end effector and/or kinematics data of the end effector (or system more generally). The portion of a model displayed on the display can change by changing the digital zoom of the representation, i.e. the zoom of the imaging device itself need not change; the change can be effected by processing performed on the representation of the surgical site.

Typically, the displayed representation permits the surgeon to see where the end effector is, and to control the end effector accordingly so as to perform the surgical procedure. Since the surgeon sees the portion of the surgical site that is displayed, rather than the body as a whole, the surgeon may become disoriented during the procedure. In other words, the surgeon may lose track of which part of the surgical site is being viewed, and/or at what orientation that part of the surgical site is being viewed. This can have implications including lengthening the time taken to perform a procedure, due to additional time being required for the surgeon to correctly orient themselves before continuing. The present inventors have realised that additional information may be provided to the surgeon (and/or to other members of operating room staff), preferably during the surgical procedure. Such additional information may be provided by augmenting the representation of the surgical site, and/or by augmenting the display of the representation of the surgical site.

It may additionally or alternatively be desirable to show on a display information relating to the state of at least a portion of patient anatomy such as an anatomical structure at the surgical site, and/or information relating to a state of health of a patient undergoing a procedure. For example, the information can be shown on the same display as the representation of the surgical site. The information can be used to augment the display of the representation of the surgical site. Such information need not be provided on the same display as the representation of the surgical site. The information may be provided on, or as part of, the representation of the surgical site and/or separately from the representation of the surgical site.

As will be explained in more detail below, the information can, for example, comprise information relating to a heart rate of a patient, a respiratory rate of a patient, movement of at least a portion of the anatomy of a patient, a measure of tissue perfusion of at least a portion of an anatomical structure, a measure of blood flow and/or oxygen delivery of at least a portion of patient anatomy or at least a portion of an anatomical structure, and so on. Suitably the information comprises an indication of a state of health of a patient, such as whether or not an identified parameter relating to patient anatomy is within an acceptable range.

Augmentation

Augmenting the representation of the surgical site can permit the inclusion of visual aids to a user such as a surgeon, which can for example aid in orienting the displayed representation of the surgical site. In examples discussed herein, 'orienting' suitably refers to working out or gaining an understanding of the orientation of the displayed representation. 'Orienting' can include appreciating what orientation the displayed representation is in. The approach of the present techniques can enable a surgical procedure to be completed more quickly, and or more accurately. Augmentation may provide an enhanced human-machine interaction, such as between a surgeon using the system to control an end effector and the operation of the end effector, or of the robotic system in general. As will be explained herein, such augmentation can enable users of the system to perform technical tasks more repeatably, more reliably, and/or more quickly, and so on.

Augmenting the representation of the surgical site can permit one or more health indicators to be displayed to a user such as a surgeon. Such augmentation may provide an enhanced human-machine interaction. The augmentation may enable a surgeon to more quickly determine parameters of anatomical structures relevant to a procedure being carried out, and to perform the procedure more quickly, more accurately, more safely, and so on.

Augmenting the representation of the surgical site can be done before, during and/or after a surgical procedure. Optionally, at least one augmentation is displayed on or as part of the representation during a surgical procedure. In some examples this can enable a user such as a surgeon to more accurately orient the representation in real time as a procedure is performed.

Augmentations can relate to one or more of a path taken by a surgeon through a site (e.g. by one or more end effector controlled by the surgeon), actions taken at one or more points at the site, features present (or absent) at particular locations in the site, movement of portions of the site, and so on.

Augmentations may be added automatically or in response to user input. Where augmentations are added in response to user input, the user may specify a part of the augmentation and another part of the augmentation may occur automatically. An example of this is feature identification. A processor such as an image processor may monitor the representation of the site and determine which features are present, or are likely to be present in the representation, or in the portion of the representation displayed. The image processor, or another processer operating in dependence on an output from the image processor, may automatically label or tag one or more determined feature. Alternatively, a user may indicate a feature, and the system may automatically select the label or tag to apply to that feature, for example in dependence on an automatic feature determination, such as by image recognition or image matching. The label or tag may comprise a measure of confidence, for example a probability measure, and/or a statement of confidence in respect of the feature.

The above example illustrates one use of the present techniques. It is possible for a user to tag or identify a feature such as an anatomical feature in a displayed image feed or a model of a surgical site. An augmentation can be added to the representation in dependence on a user input. For example, the user input can indicate the feature, or the location of the feature, to which an augmentation is to be added. The user may also indicate or specify the nature of the augmentation which is to be added, for example a name or label for the augmentation, and/or the type of augmentation.

In a surgical robotic system, the position of portions of the surgical robot within 3D space are typically known. For example, the location in 3D space of an end effector is known, or can be determined based on kinematic control information. Such kinematic data is already present in the system, so there may be no need to calculate additional kinematic data. Thus, the present techniques can advantageously make use of existing information in the system to provide additional benefits to users of the system. The augmentation may be an augmentation in 3D space relating to the representation of the surgical site. Where the representation moves in the display, the associated movement of the augmentation can take account of depth, rotation and/or lateral translation, and so on. This approach can give an increased accuracy of the location of the augmentation, and so an increased accuracy of interactions with the system that are based on the augmentation.

In one example, a user such as a surgeon may wish to indicate a position on an anatomical feature to make an incision or to insert a stitch. This can be useful where a surgeon finds a suitable location for the incision or stitch, but may wish to perform another task before making the incision or inserting the stich. Enabling the surgeon to add such an augmentation enables the surgeon to return to the location indicated by the augmentation quickly and accurately. The location of such an augmentation relative to a current location can aid in navigating through the surgical site and/or in orienting the representation of the surgical site. For example, viewing such augmentations on a displayed portion of the representation can enable a user to quickly and accurately determine the part of the site that is being displayed, facilitating a more efficient human-machine interaction. In the context of a surgical procedure, this can reduce the operation time, by permitting the surgeon to minimise time required to re-locate identified locations. Reducing the operation time is beneficial to patients, as it can reduce the risk of complications and aid recovery time. Reductions in operation time may be beneficial to patients and hospitals, because this can lead to an increase in the number of operations that may be performed, which may in turn lead to reductions in per-operation cost.

The augmentation(s) need not be displayed on or as part of the representation. For example, an augmentation may be added to one portion of the representation, then the displayed image changed (such as by zoom or panning of the imaging device and/or the representation) such that the augmentation(s) are no longer visible on the display. In this case, the system can be configured to indicate the presence and/or location of the augmentation(s) by adding a further augmentation, which may be of a different type, to the representation or to the displayed portion of the representation. Such an augmentation may be indicative of the direction and/or distance to or towards a feature of the representation, such as another augmentation and/or an anatomical feature in the representation. This will be described in more detail below.

In some examples, an action may be performed automatically, or in an assisted manner. For example, a common action such as tying a knot may be started by a surgeon, and the remainder of the action can be completed automatically so as to assist the surgeon. Such assisted actions are useful in repetitive movements or actions. The augmentation may be provided at a location where the automatic action is to be performed, or where assistance in performing the action is required. For instance, the surgeon can indicate one or more locations at which a knot is to be tied, and/or indicate to the system part-way through tying a knot that assistance in tying the knot is required. Once an assistive action such as tying a knot has been performed, a pre-existing augmentation may be modified to indicate that an assistive action has been performed. Additionally or alternatively, a new augmentation may be provided to indicate that an assistive action has been performed. The location of the new augmentation can provide an indication of where the assistive action was performed.

The identification of suitable locations (in the most appropriate places, orientations, spacings from one another), for example locations at which a surgeon may perform a task and/or at which the system may perform an assistive action, is suitably done by a surgeon. In some examples, the identification of suitable locations may be performed automatically. Such automatic identification may be performed in dependence on previously identified locations, for example locations which are contained in a model of the surgical site. The model may be built up by considering one or more previous procedures. Hence the automatic identification may benefit from a combined knowledge of earlier procedures, which may have been carried out by the same or another surgeon or surgeons compared to a procedure about to be carried out. In this way, a more junior surgeon may benefit from the knowledge of more experienced colleagues, without those more experienced colleagues needing to be present during the procedure or to be directly consulted before the procedure. The automatic identification of locations may be subject to confirmation by the user of the system. For example, the system may suggest optional locations. The suggested optional locations may be associated with a confidence factor, which can be indicative of the confidence that that suggested optional location is appropriate for the current procedure. The confidence factor may be determined in any appropriate way. In some examples, the confidence factor may be determined by determining a similarity between a previous procedure and the current procedure and/or a similarity between a model used in a previous procedure and the model used in the current procedure. The confidence factor may be determined in dependence on the user who performed one or more of the previous procedures. For example, a confidence factor may be higher, indicating a greater confidence, where it is based at least in part on a procedure carried out by a relatively more experienced surgeon.

The surgeon may indicate the locations, for example by identifying locations and/or by confirming suggested locations, such that the system can augment the representation of the surgical site accordingly. Where actions are to be performed autonomously, or partly autonomously, the surgeon can then indicate to the system that such at least partly autonomous actions may be performed.

A tag or augmentation may be added manually or automatically. Automatic augmentation may occur in dependence on image recognition. This will be discussed in more detail below. The augmentation may be added in dependence on an indicator. The indicator may be displayed on the display. The indicator may comprise a cursor or other pointer. The indicator may indicate a point or region of the display. For example, the indicator may be in the form of a shape such as a circle, an interior part of which is indicated by the indicator. The indicator may comprise an outer edge that appears solid and/or coloured on the display, for example the circumference of a circular indicator may be a solid black or white line. The outer edge may flash to highlight the edge. The indicator may have a different colour, contrast, 3D appearance and/or focus compared to a remainder of the display. For example, the interior of an indicator shape may be in colour, and the exterior of the indicator may be in black and white. In some examples, the interior of the indicator may be emphasised by being in focus whilst the exterior of the indicator may be out of focus. Any other suitable way of highlighting the indicator may be used.

An augmentation may be given a label. The labelling of augmentations may occur manually, automatically or some combination of manually and automatically. For example, once an augmentation has been added, a label can be specified by a user. This can be done by a user entering data, for example by entering a label on a keyboard, via a voice interface, via a gesture interface, via a pointer interface such as a mouse, and/or in any other suitable way. Combinations of these approaches to entering data may be used. In some examples, a voice-responsive input device, such as a microphone, can be used to input a label. A user may speak a label aloud which can be applied to the augmentation. A label may be added to an augmentation by selecting the label from a set of possible labels. The selection of a label can be performed via a menu system. The menu system may comprise all possible labels. The menu system may comprise, or make available, a set of possible labels. The set of possible labels may be pre-selected. The set of possible labels may be selected in dependence on at least one of a user profile for the user, a surgical procedure being performed, a location of the surgical site, and so on. In some examples a user may pre-define labels for use. The user-defined labels may be in addition to system-defined labels. The labels may be associated with one or more surgical procedure, such that a sub-set of the labels may be made available for the relevant surgical procedure. For example, the label 'artery' may be appropriately available for a wide range of procedures. The label 'kidney' need not be made available where the kidney will not be visible at the surgical site of a given procedure.

Image recognition may be used to assist in labelling an augmentation. Image recognition algorithms may select a set of possible labels to apply to an augmentation. The image recognition algorithms may select the set in dependence on the model, for example the 3D model, and/or the location of the surgical site.

The label may comprise a text label and a label highlight. The text label can, for example, provide the name of the feature being augmented, such as 'kidney' or 'artery'. Any desired level of detail may be provided in the text label. The label highlight may comprise a visual indication of a point or a region of the representation. For example the edges of a feature, such as the edges of an artery or the edges of an organ such as a kidney, may be highlighted. Additionally or alternatively an interior region of a feature, for example a region bounded by edges of the feature, may be highlighted. For example, internal structures such as blood vessels may be highlighted in outline. In another example, edges of a tumour (with or without a resection margin) may be highlighted. Highlighting may be determined in dependence on one or more other imaging modality such as a pre-operative CT scan. The highlighting may take the form of one or more of an outline, shading, colouring, a change in 2D/3D appearance, differing contrast and so on. In one example, an organ such as the kidney (or that part of the organ visible in the representation) can be shaded. This can assist the user by providing a clear indication of the whereabouts of that feature, the kidney in this example, in the representation. Shading a feature may be desirable where a surgical procedure does not envisage interacting with that feature. Where a surgical procedure envisages interacting with a feature to be highlighted, an alternative form of highlighting, such as one that does not obscure the feature, may be used. The edges of the feature to be highlighted can be determined manually and/or automatically. In one example, a surgeon can guide the indicator to a point on the edge, and indicate to the system that this point represents a point on the edge of a feature. The surgeon may trace out the edge, or provide one or more points along the edge, based on which the remainder of the edge can be interpolated, extrapolated and/or otherwise determined by the system, for example by image analysis. For example, the system may be configured to determine a difference in one or more image characteristic to either side of the edge (for example one or more of colour, contrast, luminosity, depth and so on) and to trace a line through the image that follows the change in that one or more characteristic. Once the feature has been labelled, the system may perform image analysis and/or tracking to consistently label that feature as the representation changes.

The augmentation may be added or selected by a user of the system. For example, a controller, which may comprise an input device, may be configured to output an augmentation signal. The augmentation signal may be associated with the location of the indicator on the display. The augmentation signal may be indicative of the location on the display of the indicator. For example, where a user controls the controller to output the augmentation signal, the system may be configured to add an augmentation at the location of the indicator. In some examples, where a menu system is to be navigated, the location of the indicator in the menu system (i.e. a menu system value, or label) may be selected by activating the controller so as to output the augmentation signal.

The controller may be configured to output the augmentation signal in response to activation of a user control at the controller. The user control may comprise a button or switch. The user control may comprise a keyboard. The user control may comprise a resistive sensor, a capacitive sensor, a track ball, a joystick or a thumbstick, a voice sensor, a gesture sensor and/or any combination of these and other user input devices. The controller is, in some examples, configured to output the augmentation signal in response to receiving user input at the input device. The input device may comprise the user control. The input device suitably enables the user to control an indicator on a display. For example, movement of a joystick or thumbstick on the input device may cause a corresponding movement of an indicator on the display. In some examples, movement of the input device may cause a corresponding movement of the indicator on the display. For instance, a hand controller may be moved in three dimensions via, for example hand controller arm links and gimbal joints. Movement of the indicator may be based on at least one dimension of movement of the hand controller. For example, movement in two dimensions (such as those defining an x-y plane or a y-z plane) may control movement of the indicator in two dimensions on the display. This approach allows the indicator to be moved around the display by the user in an easy and intuitive manner. In one example, the movement in three dimensions of the hand controller may be used to control the positions of end effectors, and a thumbstick on one (or in some examples, both) input devices can be used to control the indicator position in the representation of the surgical site.

The controller may comprise or be part of a user console of a surgical robot.

Figure 4:
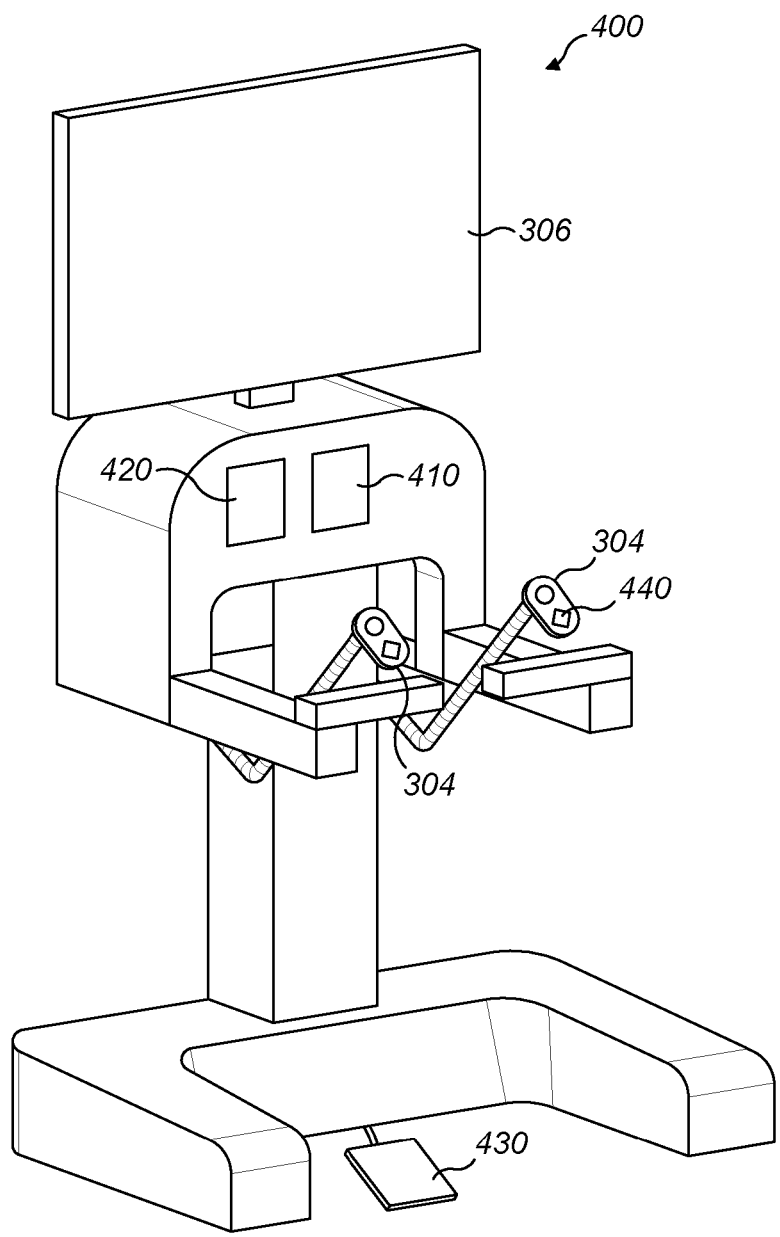
FIG. 4 illustrates a surgeon console.

An example illustration of a user console such as a surgeon console 400 is shown in FIG. 4. A user such as a surgeon can control the robot arms 302 and the instruments 320 coupled to the robot arms 302 via the input devices 304 at the surgeon console 400 and can manipulate the robot arms and/or the instruments as desired. As illustrated in FIG. 4, the surgeon console 400 comprises a contactless input device 410 which comprises at least one of a gesture sensor such as an optical gesture sensor and a voice sensor. The surgeon console 400 comprises a touchscreen input device 420. Additionally or alternatively, the display 306 may comprise a touchscreen input. The surgeon console 400 comprises a foot-operable input device 430 such as a foot pedal. One of each of devices 410, 420, 430 are shown in FIG. 4, but it will be appreciated that any numbers of any combination of these devices may be provided in other examples. Not all input devices, or all types of input devices, need be provided in all examples.

Figure 5:
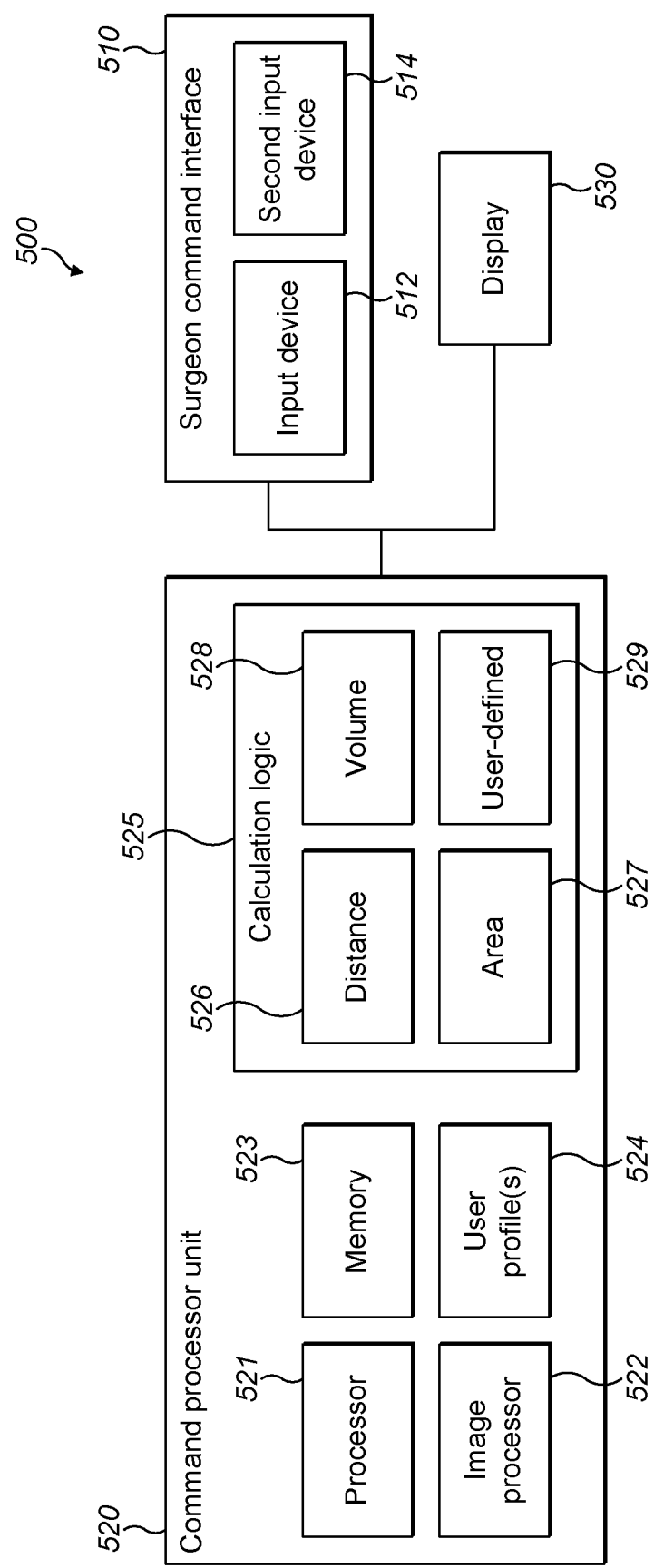
FIG. 5 schematically illustrates the configuration of a controller.

A schematic diagram of the configuration of a portion of a controller such as a user console 400 is illustrated in FIG. 5. The controller 500 comprises a surgeon command interface 510. The system further comprises a command processor unit 520 and a display 530. The command processor unit 520 is coupled to both the surgeon command interface 510 and to the display 530. The surgeon command interface 510 is configured to be operable by a user such as a surgeon. The surgeon command interface 510 permits the user to enter commands to the surgical robotic system. The user can use the command interface to control the operation of the surgical robotic system, for example by controlling one or more robot arms and/or end effectors coupled to the robot arms. The command interface 510 comprises an input device 512. The input device 512 may, for example, be an input device as illustrated in FIG. 4 at 304. Only one input device is shown in FIG. 5, but more than one input device may be provided. Typically, two input devices 512 are provided, one for use by each of a user's two hands.

In some examples, the input device can be a handheld controller for manipulation by a surgeon controlling the surgical robot. For instance, the input device can be communicatively coupled to a robot arm and instrument, whereby the position and operation of an end effector of the instrument, such as at a surgical site, can be controlled by the surgeon.

A second input device 514 is provided at the command interface 510. The second input device is, in some examples, of the same type as the input device 512. In other examples, the second input device 514 is a different type of device to the input device 512. For example the second input device 514 may comprise one or more of a voice interface, a gesture interface and a touch interface. Thus, the second input device 514 may be responsive to a voice command, a gesture and/or a touch received at the second input device. The input device 514 may, for example, be a device as illustrated in FIG. 4 at 306, 410, 420 or 430.

This arrangement permits a surgeon to use the second input device to augment a representation of the surgical site. For example, during a surgical procedure, a surgeon may use the input device to perform part of the surgical procedure. At a point in time selected by the surgeon, it may be desirable to augment that part of the representation of the surgical site at which the indicator, controlled by the input device, is located. For example, where a surgeon has just completed a stitch, the surgeon may wish to augment the representation of the surgical site at or near to the stitch. This can allow the surgeon to record, on the representation of the surgical site, the location of the stitch. This can enable the surgeon (and/or another person) to locate that location, i.e. the stitch, at a later time (for example later in the procedure or during post-procedure review). As the surgical procedure progresses, the part of the surgical site displayed on the display is likely to change. Augmenting the representation of the surgical site so as to record the location of the stitch permits the surgeon to determine the orientation or direction, and/or distance, of that location from the current location. This can be useful in helping the surgeon to appropriately orient the displayed representation, for example where the stitch is no longer displayed on the display. The provision of the second input device permits the augmentation to be added without requiring the surgeon to change the manner in which the input device is used to control the end effector. That is, the end effector need not be moved to add the augmentation. The surgeon could, for example, say 'stitch', and the second input device can detect the surgeon's voice input, determine the command (here, 'stitch') and cause a signal to be generated to cause the representation of the surgical site to be augmented accordingly. Additionally or alternatively, the surgeon may perform a gesture for detection by an input device sensitive to gestures, such as a camera. The surgeon may touch a touch-responsive input device, for example the display screen on which the representation of the surgical site is displayed. The second input device need not be controlled by the same person controlling the input device. In some examples a surgeon will control the input device so as to perform a surgical procedure. A surgical assistant, or other member of operating room staff, may use the second input device. In some examples, the second input device may take a similar form to the input device. In some examples, one or both of the input device and the second input device can be used to navigate a menu of the surgical robotic system, for example a menu displayed on the display. The menu options may be pre-configured. The menu options may be pre-configured according to one or more of: user preference, type of surgical procedure, stage in the surgical procedure, type and/or number of end effectors coupled to the system, and so on.

The second input device 514 need not be provided at the same command interface 510 as the input device 512 in all examples. For instance, the input device may be at or associated with one user console, and the second input device may be at or associated with the same or a different user console. The second input device may be configured to generate a signal. The processor may be configured to receive the generated signal from the second input device and augment the representation of the surgical site or modify an augmentation accordingly.

For instance, two surgeon control consoles may be provided, each for controlling separate robot arms (or separate sets of robot arms). For example, one surgeon console may be for controlling robot arms operating in the abdominal cavity and the other surgeon console may be for controlling robot arms operating trans-anally. It is useful for the display relating to one surgeon console to be augmented with an augmentation derived in dependence on or by the other surgeon console.

The provision of a second input device 514 of a different type to the input device 512 advantageously permits the user of the command interface 510 to effect control of the robotic system more easily. For instance, where a user is controlling two manually operable input devices 512, the user is likely to need to let go of one of these input devices to be able to control a further manually operable input device. The user can advantageously effect control of the second input device 514 without needing to relinquish control of either of the two input devices 512. For example, where the second input device 514 comprises a voice interface, the user can speak a command aloud. This can be done whilst retaining a hold of the input device(s) 512.

As illustrated in FIG. 3, the command interface is coupled to a control unit 309 for effecting control of the robot arms and end effectors of the surgical robotic system. Referring again to FIG. 5, the command interface 510 is communicatively coupled to a command processor unit 520. The command processor unit 520 comprises a processor 521. The processor 521 is configured to communicate with the command interface, or controller, 510 and to be able to control augmentation of a representation of a surgical site. The processor 521 may be configured to perform image processing, such as image recognition. Additionally or alternatively, an image processor 522 may be provided. The image processor 522 may be configured to perform image processing such as image recognition. The processor 521 and/or the image processor 522 may be configured to perform edge detection, spectral analysis and so on.

The processor 521 and the optional image processor 522 have access to a memory 523. In the example illustrated in FIG. 5 the memory is provided at the command processor unit 520. In some examples the memory may be provided elsewhere, and/or an additional memory may be provided elsewhere. Providing the memory 523 locally to the command processor unit 520 may improve memory access times. Providing the memory 523, at least in part, remote from the command processor unit 520 may enable a larger memory to be used without requiring a large physical size of the command processor unit 520. Where at least a portion of the memory 523 is provided remote from the command processor unit 520, the remote portion of the memory 523 may couple to the command processor unit 520 by one or more of a wired and a wireless connection.

The memory may store programs for execution by the processor 521 and/or the image processor 522. The memory 523 may be used to store the results of processing, and optionally intermediate processing results. The memory 523 may store a representation of the surgical site, or at least a portion thereof. The memory 523 may store augmentations in respect of the representation of the surgical site. The augmentations may be stored as part of the representation of the surgical site, or separately therefrom. In some examples, the augmentation(s) may be stored at the memory 523 at the command processor unit, and the representation of the surgical site on which the stored augmentation(s) is based may be stored at a remote memory. In some examples one or more augmentation may be stored at the memory 523 at the command processor unit, and one or more augmentation and the representation of the surgical site on which the augmentations are based may be stored at a remote memory.

The command processor unit 520 may comprise calculation logic 525. The calculation logic may comprise distance calculation logic 526, area calculation logic 527, volume calculation logic 528 and/or user-defined calculation logic 529. The calculation logic may comprise time-varying change calculation logic. The calculation logic is suitably configured to calculate one or more metric in dependence on at least one augmentation, as is described in more detail elsewhere herein.

Specifying Augmentations

The following describes examples of how an augmentation may be specified by a user.

As discussed, an indicator on the display is controllable by the controller. The indicator may comprise a pointer such as a mouse pointer. An indicator such as a mouse pointer is typically a virtual indicator, in that it is not present at the surgical site, but is added to the representation of the site, or overlaid on the representation when the representation is displayed on the display.

In some examples, the indicator may comprise a physical indicator. The physical indicator may be provided as part of the surgical robot. For instance, the physical indicator may be provided as part of the end effector. Since the end effector is viewable on the display, the end effector itself may be used as the physical indicator.

The physical indicator may comprise an indicator portion of an end effector. For example, where the end effector is a gripper tool that has a pair of jaws, the indicator may comprise the tip of the jaws in the closed position. The end effector may have an indicator mode in which the end effector can act as an indicator. The indicator mode may be entered where the jaws are completely closed, or closed past a pre-determined point. Additionally or alternatively, the user may be able to select, via for example a control at the controller, for instance a control at one or other of the input device and the second input device, between an indicator mode for the end effector and a non-indicator mode for the end effector. Suitably, the end effector remains controllable in the usual manner whether or not the indicator or non-indicator mode is selected, such that there need not be any disruption in the procedure being carried out. The jaws of the gripper (or, more generally, the configuration or operation of any other end effector) need not be in a particular configuration for the end effector to act as an indicator.

In some examples, the indicator may comprise a particular portion of the end effector. For instance, a tip of a jaw, a tip of a needle, and so on. For example, where the end effector is a gripper, the tip of the left-most jaw can act as the indicator. Here, left-most jaw' may be whichever jaw is to the left in the display as viewed by a user, or it may be a given jaw of the end effector irrespective of the orientation as viewed. The indicator portion of an end effector may be indicated as such, for example by a mark on the end effector itself (which may be a difference in colour, shape and/or configuration from another portion of the end effector) and/or virtually on the display. Indicating the indicator portion of the end effector virtually has the advantage that such indication can be changed in accordance with one or more of user preference, operating conditions, surgical procedure being undertaken, and so on.

The augmentation may be added to the representation of the surgical site at the location indicated by the indicator. For example, the augmentation may be added at the position at which the indicator is located. The indicator position may be the position on the display (i.e. in the two-dimensional screen space of the display). The indicator position may be a projection of the indicator on the display onto a feature in the three-dimensional representation.

The augmentation is suitably added in response to the output of an augmentation signal by the controller. The augmentation signal may be output by the input device.

For example, an augmentation may be added to a feature indicated by the indicator, or to the location on the feature indicated by the indicator. A user may control the indicator to be over a desired feature, such as an organ in the displayed representation. The user may cause the controller to output the augmentation signal. In response, the processor 521 may augment the representation of the surgical site, such as by adding an augmentation at the indicator location. The user may open a menu, or a menu may open automatically on addition of an augmentation. The user can navigate the menu using the controller, for example the input device or the second input device, so as to select a desired label for the augmentation. In other examples, the processor 521 or image processor 522 may determine the feature to which the augmentation has been added. This determination may be made by image recognition and/or image matching or other image analysis, for example based on a 3D model which may be derived at least in part from data derived from a scan such as an MRI scan. An appropriate label for the determined feature may then be added to the representation or otherwise associated with the augmentation. In some examples, the label may be the name of the feature, e.g. 'artery', 'kidney', and so on.

An augmentation may be added automatically by the system, for example by the processor 521. The user need not take any action for the controller to output the augmentation signal. In some examples, the controller may comprise or have access to a clock, and the augmentation signal can be output by the controller in dependence on the clock. For instance, augmentation signals may be output at a pre-selected time, or at a pre-selected frequency. This can permit data to be obtained about the time taken for different surgeons to reach a given point in a procedure, or for data to be obtained about the point in a procedure a surgeon reaches at a given time from starting the procedure. Such data can enhance post-procedure, or offline, analysis of procedures that have been carried out. Such augmentation can be done automatically, without needing user input. This approach enables the data to be obtained repeatably and efficiently.

An augmentation may be added automatically, or manually, at any desired stage in a procedure. In some examples, the system may monitor the procedure and compare the procedure being carried out with one or more previous procedure. Such a comparison may be performed continuously or periodically. A periodic comparison may use less processing power than a continuous comparison, and so may be preferred. The comparison may be performed by image processing of the representation of the surgical site in respect of the procedure being carried out and a representation of a corresponding site in respect of the one or more previous procedures. The representation of the corresponding site may be based on an average of models associated with the one or more previous procedures. Where action is occurring in the procedure, it may be preferred to perform the comparison at a relatively greater rate than when no action is occurring. Thus, movement at the site, for example of an end effector, can be taken into account in performing the comparison. The rate of comparison may be increased where the rate of movement is greater. A higher rate of comparison during periods of activity enables accurate comparisons to be made whilst saving processing power during periods of relative inactivity. The rate of comparison may be determined in dependence on robot kinematic data. For example, the rate of comparison may be determined in dependence on a velocity of a portion of an end effector, and/or on the operation of an end effector.

An augmentation may be added where a determination is made that the current procedure deviates from the one or more previous procedure. The deviation may relate to the time, or relative time, at which stages of the procedure are performed. The deviation may relate to locations at which stages of the procedure are performed. A deviation may be determined to occur when the current procedure varies from an expected behaviour, such as one expected on the basis of the one or more previous procedure or on the basis of a procedure plan (either based on a standard plan/recipe card or one written just for the current patient), by more than a threshold amount. The threshold amount may be a time period at which an action is performed. For example, where actions are performed greater than 5 seconds, 10 seconds, 30 seconds, 1 minute, 2 minutes or 5 minutes earlier or later than an expected time, it may be determined that a deviation has occurred. The threshold amount may be a distance from a predetermined location in the representation of the surgical site. For example, where actions are performed greater than 1 mm, 2 mm, 5 mm, 10 mm or 20 mm from an expected location, it may be determined that a deviation has occurred. Such an approach allows a useful comparison to be made between procedures whilst permitting differences, such as physiological differences, to be taken into account.

In some examples, the representation may be augmented where it is determined that an error condition has occurred. The error condition may comprise a robot arm and/or instrument fault. Threshold values for determining the occurrence of an error condition may be user-definable, and/or pre-set.

The augmentation signal may be generated in dependence on any desired source, for example a telematic data source. For example, the augmentation signal may be generated in dependence on determining one or more of an instrument change, change of a hand controller-arm association, change of electrosurgical mode, movement of the endoscope, re-indexing at least one hand controller, etc. The augmentation signal may be generated in dependence on a particular combination of any of the actions described herein occurring.

The augmentation signal may be indicative of a feature displayed on the display. The augmentation signal may comprise location data indicative of the location of the indicator with respect to the representation of the surgical site. For example, the augmentation signal may comprise data relating to the location of the indicator with respect to the 3D model. The controller, for example the input device, may be configured to provide the location data. The location data may be obtained in dependence on the displayed indicator.

The location data may comprise joint data, such as data associated with one or more joint of the robot arm and/or end effector. The joint data may comprise joint position data. For example the joint position data may comprise data relating to the positions, orientations and/or configurations of joints of a robot arm supporting an instrument, and/or data relating to the positions, orientations and/or configurations of joints of the instrument and/or end effector of the instrument. The joint data may comprise kinematic data. For example the kinematic data may comprise data relating to a change in position, orientation and/or configuration of one of more joint of the robot arm and instrument. The kinematic data may comprise data relating to a rate of change in position, orientation and/or configuration of one of more joint of the robot arm and instrument. The kinematic data may comprise initial position data of the one or more joints, from which the change in position occurs. The provision of such location data is particularly useful where an end effector acts as the indicator. In such cases, the 3D position of the indicator (i.e. the end effector) will be known. Thus the augmentation may be added to the representation in a highly accurate manner. This approach may also offer savings in terms of processing required, since the location data already exists in the system, and need not be recalculated.

In cases where a more accurate identification of a feature in the displayed representation is desired, it is possible to tag a feature at more than one location. The tags may be input at spaced, for example laterally-spaced, positions on the feature. In some examples, it may be desirable to change the orientation or zoom of the representation between one tag and another tag. In some examples, it may be desirable to change viewing conditions between one tag and another tag. Viewing conditions may comprise whether the view is a 2D view or a 3D view, image contrast, image colouring and/or shading, and/or whether image enhancement is present. In some examples, a feature may be indicated by one or more tags with a patient in one position, and the patient subsequently moved (such movement can comprise moving one or more limb of the patient, and/or moving the orientation of an operating table on which the patient rests, and so on). Patient movement can, in some cases, cause parts of a surgical site to move relative to one another. For example, a change in orientation of the patient may cause organs to move due to differing gravitational effects. With the patient in a new position, the same feature may be tagged by one or more tags. Tagging features in this way can assist system robustness against patient movement or other similar effects. For example, tagging a feature at different patient positions may assist in enabling that feature to be tracked during a procedure, during which a patient may change positions. Image processing may be performed to identify whether the two (or more) tagged locations are part of the same feature, for example points spaced along an artery or points at different positions on a kidney. Where one point is on one feature (say on an artery) and another point is on a different feature (not on the artery), the system may prompt the user to tag one or more further points. A feature may be selected as the feature at which augmentation is desired in dependence on the relative number of tags at that feature compared to tags that are not at that feature. In this way, an inadvertent tag need not be removed or adjusted by a user, which may be time consuming, but rather one or more additional tag may be made (which may be quicker for the user) to indicate the feature to augment.

Once the representation has been augmented, the augmentation may be movable, for example automatically or by a user. The augmentation may be movable by dragging and dropping the augmentation on the display. The controller may be configured to permit such dragging and dropping, for example via a computer mouse cursor, the input device and/or the second input device.

As mentioned, an augmentation may be labelled by a user, using free text, and/or selecting from a set of labels. The labelling of an augmentation may occur automatically, or at least partly automatically. For instance, the representation may be processed by the processor 521 or the image processor 522 and image recognition techniques used to suggest what a particular feature is. In some cases, there may be difficulties in using such image recognition techniques alone. This may be because the imaged surgical site may not have high enough contrast, and/or it may not be well lit. Advantageously, the present techniques permit an enhancement in image processing. A comparison can be made between the representation of the site for the current procedure, and one or more representation of a previous procedure and/or a model. The representation of the previous procedure and/or the model suitably comprise at least one labelled or known feature. Where the feature in the current representation is determined to be the same or similar to that in the previous representation or in the model, the label of that feature in the previous representation or the model may be made available for selection by a user, or automatically applied to the augmentation of the feature in the current representation. A determination as to whether a label is made available to a user for selection or automatically applied may be made in dependence on a confidence factor associated with the label. This approach permits the system to 'learn' the identities of different features by building up a database in respect of similar types of procedures and/or models of procedures. Thus the automatic labelling, or suggestion of possible labels, can be made more accurate. This can save user time in correctly labelling features. A more accurate labelling of features can increase the accuracy of tasks based on those labels.

The processor may be configured to monitor or track an augmentation and/or a feature of the representation such as an anatomical feature, for example an organ or a blood vessel. In some examples, the feature such as an anatomical feature can be determined automatically. For example the system can determine the feature by image processing. This monitoring or tracking of the augmentation and/or feature is useful where the representation of the surgical site changes. For example, a viewing position of the representation may change. This may be due to a lateral move of the viewing position, or to an angular change in viewing position, as may occur, for example, on a change in the location and/or orientation of the imaging device. Usefully, the system is configured such that the augmentation retains its position relative to the representation of the surgical site as the portion of the representation that is displayed on the display changes. For example, where an imaging device moves to the right, causing the representation based on the image output of that imaging device to move to the left on the display, the augmentation will also move to the left. The system is suitably configured so that the augmentation moves in registration with the representation of the surgical site, i.e. the system is configured so that the augmentation moves together with the representation. For instance, where an augmentation is added to a particular feature in the representation, the augmentation suitably moves together with movement of that feature. Such movement of the feature may occur on a pan and/or zoom change with respect to the representation of the surgical site. Movement of the feature may occur in other ways. For example, the surgical procedure may involve moving the feature. The feature, such as an organ, may move due to one or more of breathing, heartbeat and gravity (e.g. when a patient table is adjusted).

As mentioned above, an augmentation may be added manually and/or automatically. An augmentation may be added in dependence on determining that an augmentation criterion is satisfied. The processor 521 may be configured to determine whether or not the augmentation criterion is satisfied.

The augmentation criterion may comprise determining whether a surgical instrument is attached to the system, detached from the system, whether the surgical instrument is operated by the system and/or whether there is a change in state of the surgical instrument. The augmentation criterion may comprise determining that there is an image recognition signal indicative of an image recognition match in the representation of the surgical site. For example, where a feature in the representation is determined by image recognition to be a particular feature, such as a kidney, it is useful for the occurrence of such an image recognition match to trigger the augmentation of the representation accordingly.

The augmentation criterion may comprise determining that there is an error signal indicative of an error associated with the surgical robotic system. The augmentation criterion may comprise determining that a particular time has been reached, or that a particular time has elapsed. More generally, it may be determined, for example by the processor 521, whether the augmentation criterion is satisfied in dependence on a time signal. For example, an augmentation criterion may comprise a particular action occurring at a particular time, or within a particular time frame. This may include a stitch or a series of stitches being made within a given time period.

The time signal may comprise a signal indicative of the time in the day. The time signal may comprise a signal indicative of the time elapsed since the start of a procedure, and/or a pre-defined point in the procedure. The pre-defined point can, for example, be the start or end of a cutting procedure, the start or end a suturing procedure and/or the start or end of an electrocautery procedure. The time signal may comprise an indication of the duration of a procedure, for example one or more of a cutting, suturing and electrocautery procedure.

The augmentation criterion may comprise determining that there is a change of a user of the surgical robotic system. A signal indicating a change of user can be indicative of a surgeon controlling the input device pausing the procedure, for example by clutching out the input device so as to decouple the input device from active control of the end effector, and the procedure being resumed by another surgeon. The signal indicating a change of user can be indicative of a surgeon at one console taking over from a surgeon at another console. This could occur during a surgical procedure, or at a break in a surgical procedure.

Determining that there is a change of a user may be made in dependence on a signal such as a user-change signal. It may be determined that a user of the system has changed in dependence on a login or registration associated with the user of the system. It may be determined that a user of the system has changed in dependence on a recognition signal associated with a user. The recognition signal may be output from an imaging device or visual processor, which may be configured to perform facial recognition to identify a user, for example from a group of users, and/or to perform pattern recognition on for instance a 2D code such as a QR code. The recognition signal may be output from a wireless receiving device configured to detect a wireless signal. The wireless receiving device may be configured to detect WiFi™ signals, Bluetooth™ signals and/or radio frequency signals such as RFID signals. A device carried by a user that emits at least one of these types of signal can be used to distinguish between users, and optionally to identify a particular user.

Augmenting the Representation 'Offline'

An augmentation may be added during a procedure, as described in examples above. An augmentation may additionally or alternatively be added before or after a procedure.

An augmentation may be added before a procedure is started, for example in a planning phase. Before the procedure is started there will not be a 'live' image feed from an imaging device at the surgical site. Preferably therefore, before a procedure is started, an augmentation is added to a model such as a 3D model of the site. Such a 3D model may be generated in one of several ways. For example, the 3D model may be derived from a scan such as an MRI scan. The 3D model may be derived from a stereotype, which may be selected according to one or more patient-related parameter. The 3D model may be derived from more than one stereotype. For example, the 3D model may be derived from a weighted combination of different stereotypes.

The controller is suitably configured to be able to navigate through the model so as to visualise the expected representation during the procedure. For example, this can be done by the input device and/or the second input device.

In the planning phase, augmenting the representation of the surgical site is useful so as to be able to identify possible areas of interest and/or the location of expected surgical interventions. In such a planning phase, the augmentations may be added by a surgeon or other medical practitioner. For example the augmentation may be added by a trainee surgeon or a nurse. Such augmentations added in the planning phase need not be that accurate. It may be sufficient to indicate a general area or feature. Such augmentations can indicate an approximate location in the overall surgical site, for example by identifying key features and/or the direction of key features such as blood vessels, organs, tumours, safety/resection margins and/or bone structure. Such indications may reduce the time needed by a surgeon during a procedure. For instance, by assisting the surgeon to locate themselves within the surgical site, the augmentations can save the surgeon time and/or effort. This can help in reducing the overall time required for the procedure, which can have advantages for both the patient and the hospital, as discussed elsewhere herein.

During the procedure, augmentations may be added to highlight areas of interest. These can include points to which the surgeon may wish to return during the procedure. This could be because the surgeon has noticed something unexpected which warrants a more detailed check. Such augmentations may indicate a single point of interest (such as an organ), or multiple points of interest (for example multiple organs or multiple points on the same organ).

An augmentation may be added by the surgeon to indicate an area of higher risk or danger. For example, it may be desirable to highlight, by means of an augmentation, the location of a blood vessel such as an artery. This can assist the surgeon in avoiding the blood vessel, and so can reduce the risk of causing unintentional bleeding during a procedure.

Augmentations may be added to indicate way points in a procedure. Such way points may be useful in guiding a user (such as a trainee or less experienced surgeon). This approach can enable a user to more quickly retrace a traversed path, which, in turn, permits a reduction in the time needed to complete a procedure. Way points may be useful in guiding a trainee or less experienced surgeon either during a live procedure, or during a simulation of a live procedure.

An augmentation may be added at the location of a suture, a cut, an electrocautery operation and/or a grip point of tissue. In general, an augmentation may be added at a point at which an end effector is or becomes operational. Augmenting the representation of the surgical site in this way permits activity sites to be tracked. The 3D location of these activity sites can be determined, based on the augmentations. This can permit later analysis of the procedure, or of the particular activity during the procedure.

Augmentations may be added after a procedure has been completed. Such augmentations may be added on a recorded feed of the procedure and/or on a model constructed in dependence on data obtained from or during the procedure. The augmentations may indicate possible areas for improvement. Adding such augmentations after the procedure has been completed means that a review of the procedure may be carried out in a less stressful environment than during the procedure itself. A greater level of analysis may therefore be performed than might be possible during the procedure. In some examples, the augmentations can indicate an optimum location and/or spacing of suture sites. Such augmentations can raise awareness amongst users of potential issues which might occur in later procedures which are the same as or similar to the procedure being reviewed. Raising awareness in this way can reduce the number of undesirable incidents in later procedures, which can, for instance, increase the efficiency of these later procedures and/or may reduce the number of complications during a procedure.

Augmentations added to the representation of the surgical site can be used in several different ways. One example of the way in which an augmentation can be used is to help in orienting a surgeon during a procedure. Augmentations permit indications to be added to the representation of where in the site the surgeon is looking. For example by labelling an organ such as the kidney, the surgeon will have a better understanding of the site, and so can control the end effectors and/or move around the site more easily. This will be discussed in more detail below.

Grouping Augmentations

Augmentations may be added to one or more group of augmentations. A plurality of augmentations may be added to a particular group of augmentations. Augmentations can be grouped according to a characteristic common to those augmentations. For example, augmentations may be grouped according to one or more of:
- the user of the system at the point at which the augmentation is added,
- the user who adds the augmentation,
- the procedure being carried out,
- the type of procedure being carried out,
- the type of feature being augmented (for example organs, blood vessels, tissue and/or bone, damage and or diseased areas),
- the feature being augmented (for example a particular organ or blood vessel),
- a point at which action is desired (i.e. a "to do" list, which might include an incision point),
- time (e.g. all augmentations added in the last hour, or the last 30 minutes), and so on.

Augmentations in different groups may be distinguishable on the display. For example, the system (e.g. the processor 521) may be configured to highlight augmentations in different groups differently. Augmentations may be highlighted by one or more of being in a different colour, by having a label with a different font and/or size, by having a different outline and by flashing or by flashing at a different frequency.

The system is suitably configured to show or hide augmentations in dependence on a group of augmentations to which a particular augmentation belongs. This increases the ease with which a user is able to identify augmentations of a particular type, and so to take action in dependence on those augmentations.

The system, for example the processor 521, may be configured to perform calculations in dependence on one or more augmentation. Suitably the calculations may be performed automatically. For example, the system may automatically count the number of augmentations added, or the number of augmentations in a particular group of augmentations. For example, a group of augmentations may relate to tendrils extending along a feature, such as the stomach. The surgeon may need to move around the site to see all the tendrils, as some may be on sides of the stomach facing away from each other. The surgeon need not add augmentations in respect of all the tendrils in one go. The augmentations may be added at different stages in the procedure, and indeed even in more than one procedure. It can be difficult to correctly remember the number of tendrils in such a situation. More than one user may have added the augmentations. It is therefore useful if the system provides a count of the number of augmentations in the, for example, 'tendril' group of augmentations.

The system may be configured to determine a distance between a plurality of augmentations, or a plurality of augmentations in a group of augmentations. The distance between the plurality of augmentations may comprise a largest distance between the augmentations, for example the distance between the two augmentations that are furthest apart from one another (in the 2D or 3D space of the representation of the surgical site). The distance between the plurality of augmentations may comprise the smallest distance between the augmentations, for example the distance between the two augmentations that are closest to one another (in the 2D or 3D space of the representation of the surgical site). The distance between the plurality of augmentations may comprise an average (e.g. one or more of a mean, mode or median) of the distances between the plurality of augmentations, or a subset of the plurality of augmentations. The distance between the plurality of augmentations may comprise the distance between subsequent augmentations (i.e. for 3 augmentations, the total distance may be the sum of the distance between the first and second augmentations and the distance between the second and third augmentations). This approach permits a user to add augmentations along the length of a feature, and the system to then determine the length of that feature.

The system may be configured to determine the orientation of a feature. For example, the system may be configured to determine the orientation of a feature in dependence on a line or lines joining two or more augmentations associated with that feature. The orientation may be determined with respect to a convenient frame of reference, for example a surgical table, a body cavity, another identified or selected feature at the surgical site, and so on.

The system may be configured to indicate a line between two more augmentations, or between a plurality of augmentations in a group of augmentations. The line may be visible on the display, and/or on another display. The indication of a line in this way can be useful for telestration. Providing telestration capabilities can be useful for teaching and/or guidance, for example during a procedure or during training in advance of carrying out a procedure. The system may be configured to indicate the line in dependence on one or more of a dot-to-dot line, joining all the selected augmentations, a best fit line and a spline based on the augmentations. The system may be configured to indicate the line in 2D or 3D.

The system may be configured to determine an area enclosed by the plurality of augmentations, or a plurality of augmentations in a group of augmentations. The area enclosed by the plurality of augmentations may comprise an area of a polygon, with an augmentation at each corner of the polygon. The area enclosed by the plurality of augmentations may comprise an area enclosed by the plurality of augmentations projected onto a feature in a 3D model. For example, the plurality of augmentations may be located on a curved feature such as an organ. The area enclosed by the plurality of augmentations may comprise the surface area of the curved feature onto which the augmentations are projected. This approach enables a determination of the surface of a feature within the representation of the surgical site that may be more useful than an area of a projection of the feature onto a 2D display.

The system may be configured to determine a volume enclosed by the plurality of augmentations, or a plurality of augmentations in a group of augmentations. The volume enclosed by the plurality of augmentations may comprise a volume enclosed by the locations of the augmentations in 3D space, for example in the 3D model of the surgical site. Determining the volume enclosed by a plurality of augmentations can permit a determination of the volume of a feature at the surgical site. For example, augmentations may be added across the surface of a tumour. The system is suitably configured to determine the size, or approximate size, of the tumour in dependence on the locations in 3D space of the augmentations associated with that tumour.

The system, for example the processor 521, may be configured to restrict entry into, or movement of an end effector in, past or near, a specified point, line, area or volume. The specified point, line, area or volume may be defined by one or more augmentation in one or more group of augmentations. For example, augmentations may be added on or along a feature such as an artery (this may be done in a planning phase). The augmentations relating to the artery may be in an 'artery' group of augmentations. Further augmentations may be added in respect of a vein (or other feature). The augmentations relating to the vein may be in a 'vein' group of augmentations. The system may be configured to restrict entry of an end effector into a volume surrounding one or more selected feature. For example, the system may restrict entry of an end effector into a volume surrounding one or both of the 'artery' and 'vein' groups of augmentations (or a 'blood vessel' group of augmentations that comprises the 'artery' and 'vein' groups of augmentations). This can reduce the risk of a surgeon inadvertently damaging the feature (here, the artery or the vein) during the procedure. The system may be configured to restrict or prevent motion of the end effector within a pre-set distance of such a point, line, area or volume. The system may be configured to provide feedback (e.g. visual and/or haptic feedback, such as an audible sound or vibration (for instance of the input device) in dependence on the proximity of a portion of the end effector to the restricted point, line, area or volume (or, in general, to any specified augmentation or group of augmentations). This approach can permit movement of the end effector more quickly than might otherwise be the case whilst reducing the chance of tissue damage occurring. Such an approach can therefore assist in speeding up procedures, which can improve patient recovery time.

Figure 6:
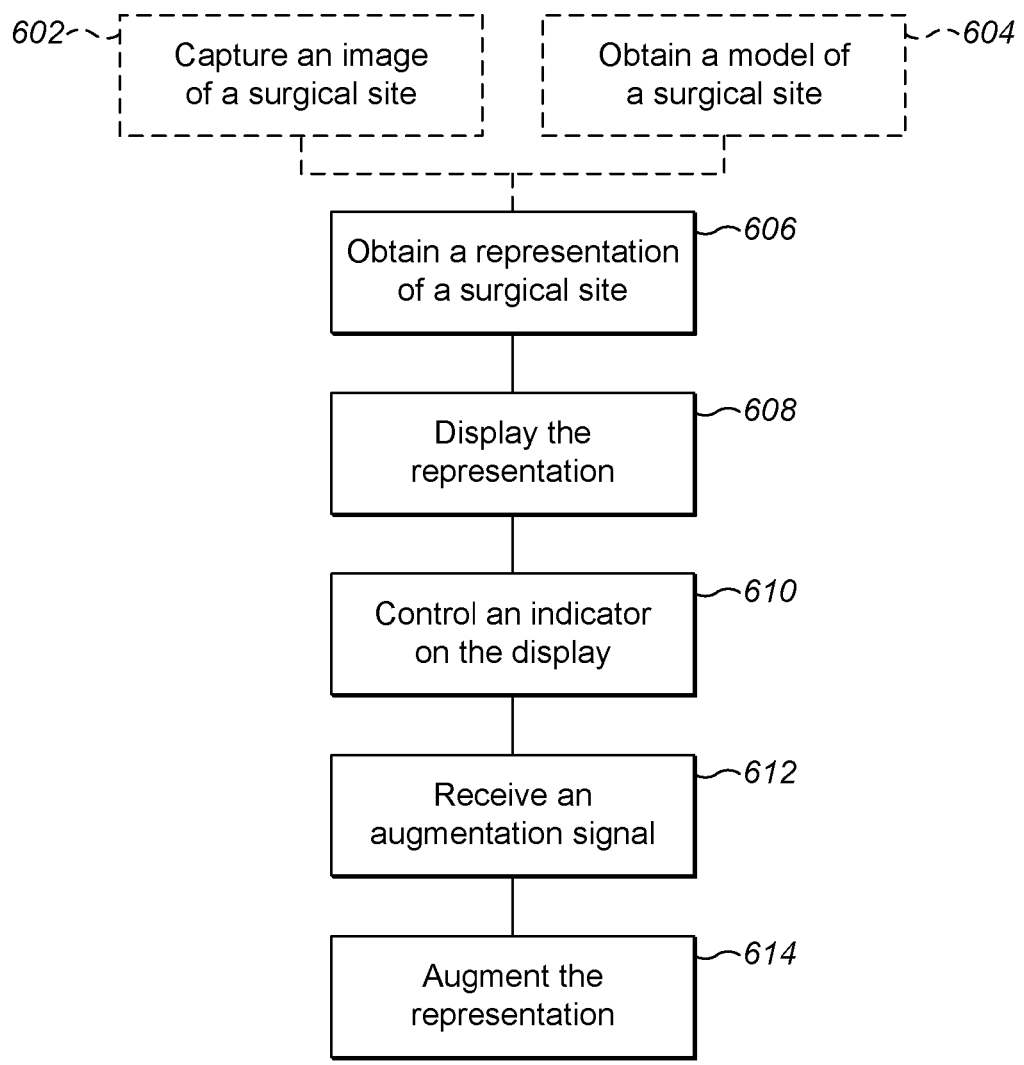
FIG. 6 illustrates a method for augmenting a representation of a surgical site.

Reference is now made to FIG. 6, showing a method for augmenting a representation of a surgical site. Optionally, an imaging device may be used to image at least a portion of a surgical site 602. Optionally, a model, such as a 2D or 3D model, may be obtained of the surgical site 604. A representation of the surgical site is obtained at 606. The representation of the surgical site may be obtained in dependence on one or both of the image of the surgical site captured at 602 and the model of the surgical site obtained at 604. At 608 the representation is displayed. For example, the representation may be displayed on a display. An indicator on the display is controlled 610. The indicator is suitably controlled by an input device at a controller. At 612 an augmentation signal is received. The augmentation signal may be output by the controller, for example by the input device. In response to receiving the augmentation signal, the representation of the surgical site is augmented 614. The representation of the surgical site may be augmented in dependence on the indicator position on the display.

Obtaining the model of the surgical site 604 may be done in dependence on a stored representation of the site. The end effector viewable on the display may comprise the indicator. The method may comprise controlling the indicator by controlling the end effector.

Orientation Augmentation

As mentioned, one or more augmentation can be provided on or as part of the representation to aid in orienting the representation. Such navigational aids can enhance the understanding of the displayed representation, and increase the speed and/or accuracy with which a user of the robotic system can use the robotic system to perform a procedure.

The processor 521 is, in some examples, configured to receive an imaging device signal. The imaging device can be configured to output the imaging device signal. The imaging device signal indicates at least one of the location and orientation of the imaging device, for example relative to the surgical site or some other appropriate frame of reference (for example a patient table (which might be movable) or an operating theatre). This enables the processor to determine the location and orientation of a portion of the surgical site that is viewable using the imaging device. I.e. the processor can determine the portion of the surgical site to which the image feed of the imaging device relates, and which can be displayed. As discussed above, the representation of the surgical site can be based on the image feed and/or a 3D model. Thus, the imaging device signal enables the processor to determine the portion of the surgical site being viewed by the imaging device. The processor may be configured to match the imaged portion of the surgical site with the 3D model. In some examples, the imaged portion of the surgical site may be the same as, or a close approximation to, the 3D model. This may be the case when organs and blood vessels in the image are in the same or approximately the same relative locations as in the 3D model. However, organs and blood vessels do not necessarily move together with one another in the same way. As a patient is tilted, for example, different organs and/or blood vessels (or indeed any other internal structure) may behave differently. The different behaviour can be at least in part due to the relative 'floppiness' (or elasticity) of the tissues. Suitably, the 3D model and/or the processor has access to data or assumptions on the floppiness of the tissues. Where there is a change, for example in patient angle, that might cause tissues to move, new positions of the tissues such as organs and blood vessels can be estimated in dependence on the floppiness values (or relative floppiness values) associated with each of the tissues. An updated 3D model can be generated based on the estimated positions. In this way, the processor may be configured to match the imaged portion of the surgical site with the 3D model and/or the updated 3D model. This approach facilitates generating the representation in dependence on both the image feed and the 3D model as it can enable the imaged view to be correctly aligned with the 3D model. The representation can be augmented in dependence on the imaging device signal. The processor can output a display signal for causing the display of at least part of the augmented representation. The system may comprise a display configured to display at least part of the augmented representation.

During a procedure, the imaging device will typically be moved. I.e. at least one of the location and orientation of the imaging device will change. The zoom of the imaging device may change. Suitably, the processor is configured to receive a further imaging device signal. The further imaging device signal is suitably indicative of an updated location and/or orientation of the imaging device, and/or indicative of an updated zoom or pan state of the imaging device. The processor is suitably configured to determine, in dependence on the imaging device signal and the further imaging device signal, a change in at least one of the location of the imaging device, the orientation of the imaging device, the zoom of the imaging device and the pan state of the imaging device. The processor may be configured to update the augmented representation in dependence on the determined change. The processor may be configured to update the augmented representation by updating the augmentation applied on or to the representation.

The representation can be augmented based on a feature of the representation, such as an organ, a blood vessel, or more generally one or more anatomical feature, and/or site of one or more of a stitch, an incision, an electrocautery action, and so on. The augmentation can indicate an orientation of the representation of the surgical site. The representation can be augmented based on another augmentation, for example an earlier-added augmentation. That other augmentation can be based on one or more anatomical feature. For example, the system may be configured to detect the presence in the representation of an anatomical feature. This detection can be performed by image processing, such as image matching and so on. In an illustrative example, the system can identify that a kidney is present in the representation (whether or not it is viewable on the display—for example, the portion of the representation being viewed may not comprise the portion of the representation that comprises the kidney). The kidney may be labelled as such, for example in accordance with one or more techniques described herein. Such a label can be added as an augmentation (again, whether or not viewable on the display). The representation may be further augmented based on this augmentation (i.e. based on, in this example, the 'kidney' label). In another example, the representation can be augmented in dependence on the determination that the kidney is present in the representation without first needing the representation to be augmented in respect of the kidney.

The augmentation indicating the orientation of the representation can take one of several forms. The augmentation can indicate the orientation by indicating a 'global' orientation of the representation, such as by indicating one or more of an upwards direction (e.g. against gravity or perpendicular to a patient table) and a direction towards a portion of the surgical site as a whole or a portion of a body (e.g. towards a trocar insertion location or towards a patient's head). The augmentation can indicate the orientation by indicating a 'local' orientation of the representation, such as by indicating the location of an anatomical feature, for example an anatomical feature that may move relative to the surgical site as whole. For example, an organ (or other anatomical feature) may move during a procedure. The organ may move due to gravity as the patient moves. The organ may move due to breathing. The organ may be moved by the surgeon. In some examples, the augmentation can point towards, or otherwise indicate, a feature that is 'off-screen', i.e. is not part of the displayed representation.

Figure 10:
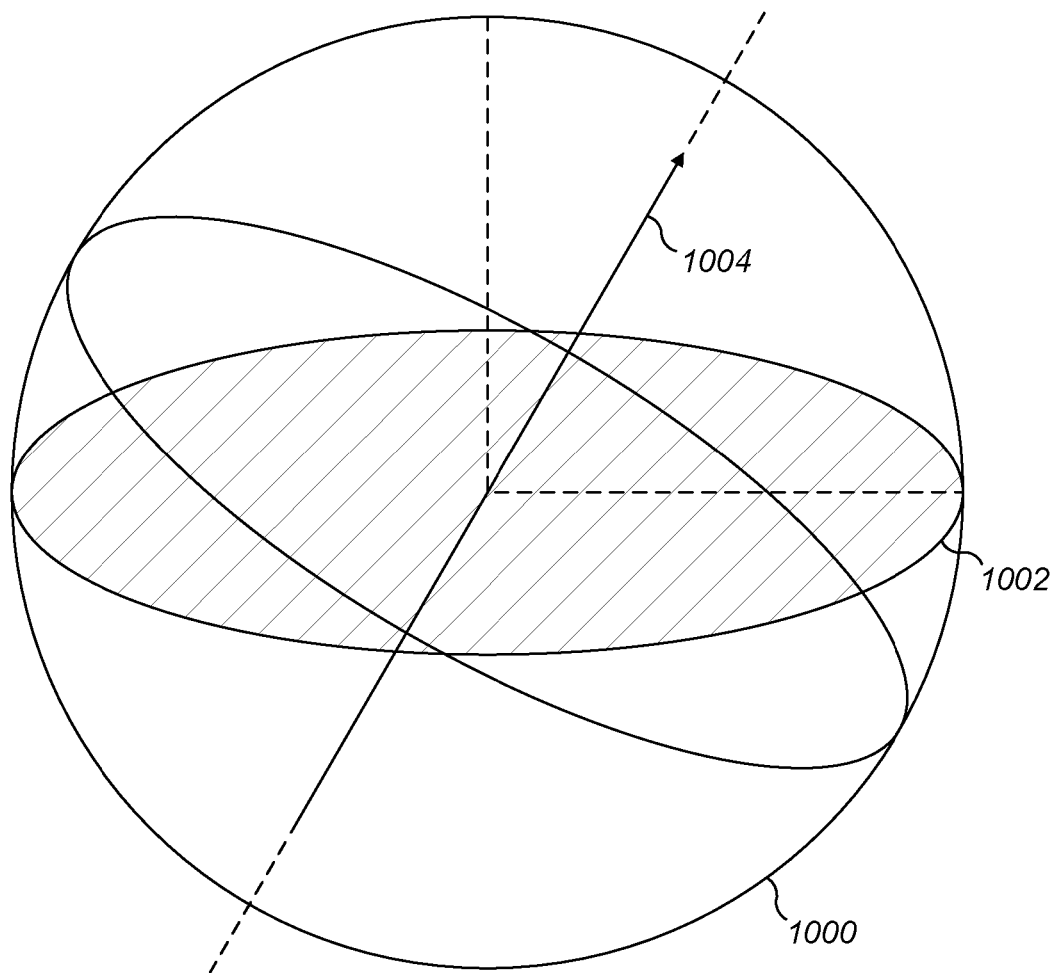
FIG. 10 illustrates another example of an augmentation

An augmentation, for example one indicating the 'global' orientation, can comprise an artificial horizon. An example of this is illustrated in FIG. 10. For example a line or plane 1002 (such as on a 3D augmentation) can indicate a level line or plane. An augmentation can comprise an indication 1004 of the direction and/or distance towards a portion of the surgical site (such as, in the example mentioned above, a trocar insertion point) or more generally to a feature of interest. For example, an arrow 1004 may be provided that points towards the feature of interest. The arrow may be provided in 2D or 3D. In some examples both the line or plane and the arrow may be provided. For example, the augmentation may comprise a sphere 1000, a plane 1002 may rotate within the sphere to indicate a gravitationally level plane, and one or more arrow 1004 may be provided within the sphere (for example a radial arrow extending between the centre of the sphere and an outer surface of the sphere) indicating a direction towards a feature of interest. The sphere may be illustrated in any convenient manner. The sphere may be transparent. The sphere may be indicated by one or more lines of longitude and/or latitude.

The processor can be configured to determine at least one of the direction and distance to the feature of interest. The distance to the feature of interest can be determined in dependence on a determination of the projected boundary of the screen onto the representation, and/or the 3D model on which the representation is based. The distance to the feature of interest may be determined in dependence on an anatomical model, for example the 3D model. The distance to the feature of interest may be determined in dependence on the location in the model of one or more augmentation. For example, where an augmentation has been added that is associated with a given feature, such as a blood vessel, the location of that augmentation may be taken as indicating the location of the associated feature, e.g. of the blood vessel. A distance from some other point (such as a boundary of the projection of the screen onto the representation) to the location of such an augmentation may therefore be taken as the distance to that associated feature.

The augmentation can comprise an indication of the distance towards the feature of interest. The distance may be measured from a point on the edge of the screen (i.e. a point at the edge of the displayed portion of the representation), from the centre of the screen (or displayed portion of the representation) or from any other point as desired. The distance may be measured to the closest edge of the feature of interest, to a central point of the feature of interest, to a point mid-way between the closest and furthest edges of the feature of interest, or to any other point as desired. Preferably, the distance is measured as the distance from the point at the edge of the displayed portion of the representation closest to the feature of interest, to the edge of the feature of interest closest to the displayed portion of the representation. I.e. the distance may be determined as the shortest distance between the displayed portion of the representation and the feature of interest. The portion of the feature of interest that is closest to the displayed portion of the representation may change as the location, orientation, zoom and/or panning of the imaging device changes. The processor may be determined to automatically update the distance determination accordingly. The augmentation can comprise a text label providing the distance to the feature of interest, for example in millimetres. Any other unit may be used. The unit of measurement, and/or the accuracy of the measurement can be selectable, for example user-selectable. The unit of measurement to use, and the accuracy at which to display that measurement may be pre-set in a user profile.

Thus, where a feature of interest is not viewable in the displayed portion of the representation, the augmentation can provide an indication of where that feature of interest is located. This indication can include the direction and distance to that feature of interest. This can enable a user such as a surgeon to get their bearings more quickly when presented with the representation, and/or reduce the risk that they will lose their bearings when navigating through a surgical site (where such navigation may include translational and/or rotational motion within the 3D site).

The feature may be considered to be not present in the displayed portion of the representation where it is not visible on a display displaying part of the representation. The feature may be considered to be not present in the displayed portion of the representation where it is occluded by another feature in the representation and/or outside the field of view of the displayed representation.

More than one orientation augmentation may be provided. Each such augmentation may point towards, or otherwise indicate, a respective feature of interest. More than one such augmentation may point towards, or otherwise indicate, the same feature of interest. For example, where two such augmentations are provided, one at each of the right-hand and left-hand upper corners of a display, the augmentations can together provide information additional to that provided by a single augmentation. For example, by a comparison of the relative distances between each augmentation and the feature of interest, it can be readily ascertained whether the feature of interest is centrally located (with respect to the display) or located to one side or the other. Such combinations of augmentations may therefore be used to gain a more accurate orientation of the representation.

Figure 7:
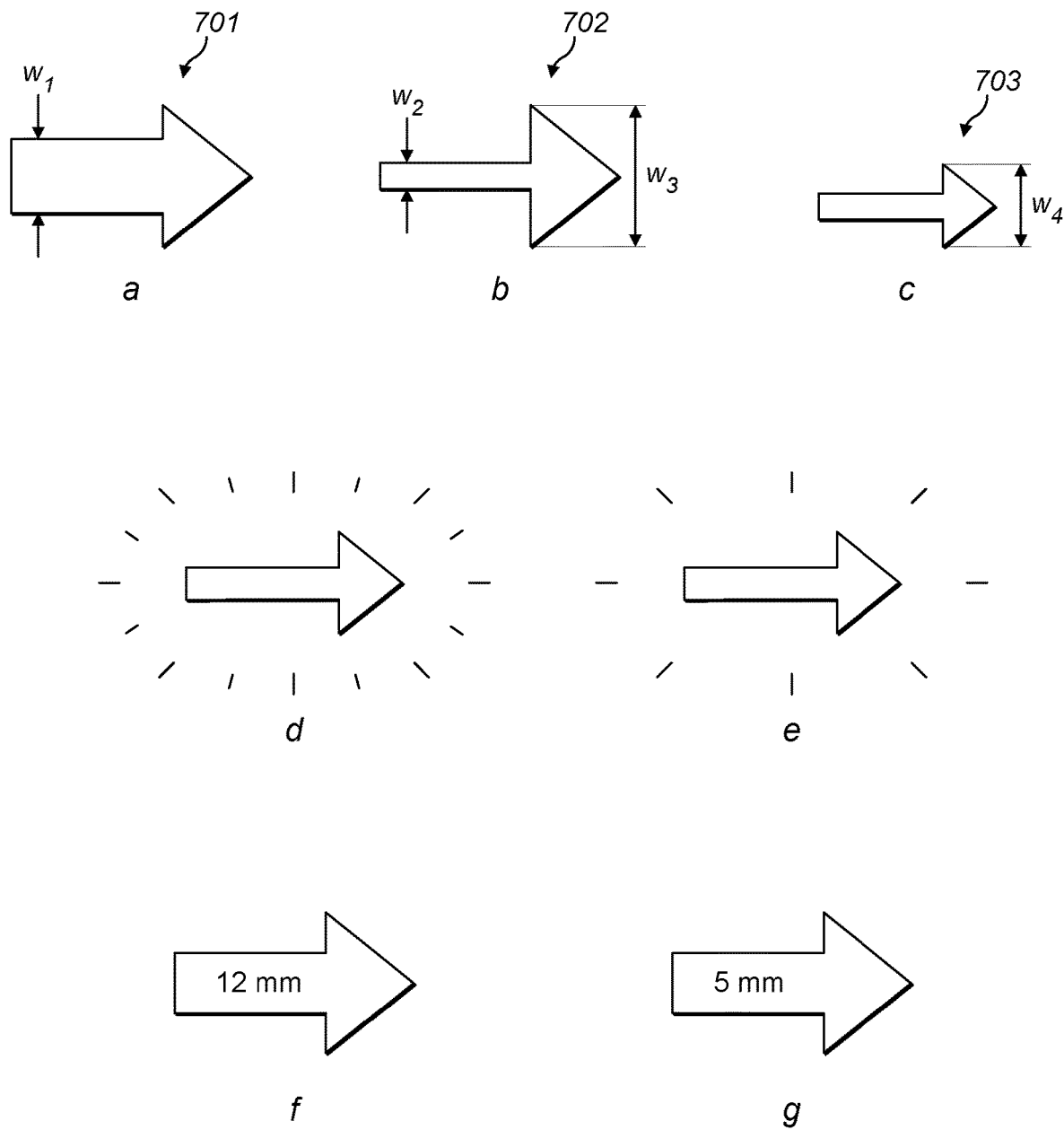
FIG. 7 illustrates examples of augmentations.

The augmentation may comprise an indication of the distance towards the feature, e.g. the distance between the edge of the screen and the feature (e.g. the closest part of the feature to the screen edge). The indication of the distance towards the feature can be provided in any convenient manner: flashing, frequency of flashing, colour, size, shape, outline, transparency, translucency, and/or any one or more of these and/or other visual features of the augmentation. The augmentation can be selected or displayed in dependence on the determined distance. Some examples of augmentations that can indicate distance to the feature of interest are illustrated in FIG. 7.

FIG. 7*a* illustrates an arrow 701 that can point towards the feature of interest. The arrow in FIG. 7*a* has a shaft of width w1. FIG. 7*b* illustrates another arrow 702 that can point towards the feature of interest. The arrow in FIG. 7*b* has a shaft of width w2. w1 is greater than w2 which can indicate that the distance from arrow 701 to the feature of interest is greater than the distance from arrow 702 to the feature of interest. In some examples a relatively greater arrow width can indicate a relatively shorter distance to the feature of interest.

Another feature of the augmentation that can change to indicate distance to the feature of interest can be seen by a comparison of the arrows in FIGS. 7*b* and 7*c*. The arrow 702 in FIG. 7*b* has an arrowhead of width w3. The arrow 703 in FIG. 7*c* has an arrowhead of width w4. w3 is greater than w4 which can indicate that the distance from arrow 702 to the feature of interest is greater than the distance from arrow 703 to the feature of interest. In some examples a relatively greater arrowhead width can indicate a relatively shorter distance to the feature of interest.

The width of the arrow shaft and/or the width of the arrowhead can be based on the distance to the feature of interest. For example, the width of the arrow shaft and/or of the arrowhead can be proportional or inversely proportional to the distance to the feature of interest. In some examples, the width of the arrow shaft and/or of the arrowhead can be linearly, inverse linearly, logarithmically, or inverse logarithmically proportional to the distance to the feature of interest.

A decreasing width of the arrow shaft and/or arrowhead can indicate that the feature of interest is getting closer to the edge or border of the display. A 'zero' width of the shaft and/or arrowhead can indicate that the feature of interest is at the border. The augmentation (here, the arrow) can be removed from the display when the feature of interest appears on the display. In some examples, an augmentation or tag which indicates the feature of interest can replace the arrow (or other 'off-screen' augmentation) as that feature of interest appears on screen. In some examples, as a feature of interest moves off-screen, the tag associated with that feature can be replaced by the 'off-screen' augmentation indicating the direction and/or distance to that feature.

Suitably the augmentation indicating the distance and/or direction of the off-screen feature of interest is updated dynamically, for example in response to movement of the imaging device and/or patient tissues.

Other aspects of the size of the augmentation may change to indicate the distance. For example, the size of the augmentation as a whole may increase where the determined distance is greater. In other examples, the size of the augmentation may decrease where the determined distance is greater. The processor may be configured to modify the size of the augmentation in dependence on the distance. The processor may be configured to modify the size of the augmentation within one or both of a minimum size and a maximum size. The minimum size and/or the maximum size may be selectable, for example user-selectable.

In some examples, the processor is configured to remove the augmentation when the feature of interest is determined to be visible on screen, e.g. when the distance from the edge of the screen to the feature of interest becomes zero. In some examples, the processor is configured to remove the augmentation when the feature of interest extends a distance inside the screen boundary. Taking this approach can mean that the feature of interest is visible and potentially also recognisable by a user before the augmentation is removed. The distance inside the screen boundary of the feature of interest at which the augmentation is removed by the processor can be pre-set and/or selectable, for example user-selectable. The distance inside the screen boundary of the feature of interest at which the augmentation is removed by the processor can be dependent on the nature, type, and/or classification of the feature of interest (e.g. where the feature is not immediately identifiable, it may be desirable to ensure that more of that feature is visible on screen before the augmentation is removed), and/or the procedure being performed (e.g. different actions may be selected for different features, depending, for example, on how critical each is to that particular procedure). In some examples, data from at least one previous procedure, optionally including data relating to one or more outcome from that procedure, can be used to determine features of interest, when to augment the representation in relation to a determined feature of interest and/or when to remove the augmentation in relation to a determined feature of interest. For example, where such data indicates confusion as to what a particular feature is (e.g. mistaking a given feature for another feature), that feature can be selected for augmentation and/or the augmentation for that feature can be retained for longer than an augmentation for another feature.

FIGS. 7d and 7e illustrate another visual property of the augmentation that can vary with distance to the feature of interest. In the illustrated examples, the augmentation is an arrow. Other shapes can be provided as or as part of the augmentation. FIGS. 7d and 7e schematically illustrate an augmentation flashing at different frequencies. The augmentation can be caused, for example by the processor, to flash at a frequency or relative frequency that indicates the distance to the feature of interest. For example, a relatively higher frequency of flashing can indicate a relatively closer (or, in other examples, further away) feature of interest.

The augmentation may comprise a text label. For example, where the augmentation comprises an arrow, the text label may be provided along a length of the arrow, overlapping with the arrow, adjacent the arrow and so on. FIGS. 7f and 7g illustrate examples of arrows on which text labels showing the distances to the features of interest are displayed. Where the augmentations comprise other shapes, text labels can similarly be provided. The text label can comprise a description of the feature, for example 'kidney'.

Where the processor is configured to remove the augmentation indicating the direction and/or distance to the feature, the processor can be configured to retain the label such as the descriptive label in respect of that feature. For example, where a kidney is off-screen, an augmentation can be applied to the representation indicating the distance and direction to the kidney. Once the kidney appears on screen, the augmentation can comprise just the label 'kidney', the remainder of the augmentation having been removed.

Suitably, the processor is configured to determine the augmentation in dependence on a feature that is not present in a displayed portion of the representation. E.g. the augmentation is determined in dependence on a feature that is off-screen.

In some examples, the processor is configured to determine the augmentation in dependence on augmentation data. The processor can be configured to receive the augmentation data. The augmentation data can comprise data associated with the representation. Such data associated with the representation may be stored with or as part of the representation. Such data can comprise tagged (or labelled) features. Such data may be based on or comprise data generated during a planning phase and/or one or more previous procedure. For example, the data associated with the representation can comprise data obtained in dependence on one or more previously performed procedure that is of the same or similar type to the procedure being performed or planned to be performed. In some examples, the data associated with the representation can comprise data obtained in dependence on one or more previously performed procedure that was performed by the same surgeon or team.

In some examples, the augmentation data comprises data indicative of a feature in the representation. For example, the augmentation data can comprise feature labels, and/or data relating to the edges of one or more of a blood vessel and an organ.

In some examples, the data indicative of a feature in the representation is indicative of one or more feature group of a set of feature groups. A feature group may relate to one or more of organs in general, blood vessels, sites at which surgical procedures are to be performed/have been performed, sites of interest, and sites or features dependent on the procedure to be/being performed. This grouping of features can enable the orientation of the representation to be based on the features relevant to the surgeon in that procedure/at that time. This approach can enable a quicker orientation to be determined—assisting the surgeon to more quickly and effectively perform the procedure, i.e. facilitating a better human-machine interaction.

In some examples, the received imaging device signal and/or the received further imaging device signal comprises kinematics data relating to the imaging device. The kinematics data may be from a kinematics controller, for example a kinematics controller at the command processor unit 520. The kinematics controller may be part of the processor 521 or it may be separately provided. Using the kinematics data in this way enables use to be made of existing information within the system; there is no need to separately calculate the kinematic data for the purposes of augmenting the representation. This can increase the efficiency of the system, for example in at least one of speed, processing power and data bandwidth. The kinematics data is highly accurate, since the kinematics data enables movement of the surgical robot. Hence, using this same kinematics data enables a quick and accurate determination of the orientation of the representation of the surgical site. This can improve the human-machine interaction, enabling the user of the system, for example a surgeon, to quickly orient themselves during a surgical procedure. This enables the surgeon to operate more quickly and/or more accurately. This facilitates improvement in surgical procedures such as the shortening of procedures (which is good for patients and hospitals).

The processor can be configured to track the location of the feature of interest, for example the location of an anatomical feature. The processor can be configured to track the location relative to the displayed portion of the representation. The processor can be configured to update the augmented representation in dependence on the tracked location and a change in at least one of the imaging device orientation, the imaging device location, a field of view of the imaging device and a field of view of a displayed portion of the representation. In some examples, the location can be tracked by image processing of the image feed generated by the imaging device. In some examples, the location can be tracked by processing the 3D coordinates of the location in the 3D model, and tracking how the model moves relative to the imaging device. Combinations of these and other approaches are possible.

It is possible to build up a data set from one or more procedure, and to use such a data set to improve the orientation determination. In some examples, the processor can be configured to determine an orientation in dependence on a feature within the representation of the surgical site (for example in dependence on a feature in an image feed generated by the imaging device). The processor can be configured to determine an orientation in dependence on more than one feature in the representation. Building up a data set over many different procedures (which may be of the same type of procedure) enables a more accurate determination of the orientation based on a greater number of reference features and reference combinations of features. A feature or features in a representation of the surgical site, for example in an image feed, can be compared with one or more feature in the data set. An orientation can be predicted or estimated, for example in dependence on the representation and/or on one or both of the location and orientation of the imaging device. Elements of the data set corresponding to orientations within a desired range about the predicted orientation can be selected for comparison with the feature or features in the image feed. The element of the data set which best matches the feature or features in the image feed can be used to determine the orientation. For example the orientation may be determined to be a previously-determined orientation in respect of the best match. In some examples, the predicted or estimated orientation can be combined with kinematics of the imaging device to increase the accuracy.

In some examples, the processor can be configured to determine (or identify) a feature in the representation in dependence on a location and/or orientation of the imaging device. For example, the processor may determine that a feature is present in a generated image feed. The processor can determine from the location and/or orientation of the imaging device the portion of the representation that is being imaged by the imaging device. The processor may, for example in dependence on the anatomical model, determine what that feature is, and may augment the representation accordingly. The processor may determine what the feature is in dependence on a data set comprising data obtained from one or more previous procedure. The data set may comprise one or more outcome from at least one previous procedure. For example, where a feature has been identified previously and/or at least a satisfactory outcome was achieved, that identification may be used by the processor to identify the feature in the current representation. This approach enables use to be made of previously identified features, allowing account to be taken of the outcomes of the procedures in which those features were identified. It can be expected that better outcomes will positively correlate with more accurate feature identifications. Thus, focusing on features identified where outcomes are above a threshold level, such as a qualitative level, can be expected to increase the accuracy of later feature identifications and hence augmentations.

At least some anatomical features typically move within a surgical site. For example, an organ may move due to one or more of gravity, a patient breathing or being artificially ventilated, being moved by a surgeon and so on. Thus the location in the surgical site of that organ will not remain constant. The location may change in a predictable manner. For example, the organ (or more generally, the feature of interest) may be in a first location at a first time, and may be in a second location at a second time. The processor is suitably configured to determine whether the current time is the first time or the second time. The processor may be configured to identify the feature in dependence on the determination of whether the current time is the first time or the second time, and/or on the determined location of the feature.

Conversely, in some examples, the processor is configured to determine a location and/or orientation in dependence on an identified feature in the representation. For example, where the feature such as an organ is movable under the effects of gravity, where the processor determines that that feature (e.g. the organ) is in a particular location (e.g. a location to which the feature typically moves when gravity acts in a particular direction relative to the surgical site), the orientation (e.g. the direction of gravity) can be determined in dependence on that location.

A user may tag a feature such as an organ, move the patient in a known way, and re-tag the same feature. This can give an indication of the elasticity of the feature, which can allow the position of that feature to be estimated where the patient undergoes other movements.

As discussed above, features can be tagged at various times before, during and/or after a procedure. Features can be tagged in different locations relative to the surgical site. Tagging features in this way can help increase the accuracy of later determinations based on such tagging. This approach enables a data set to be built up of a range of likely locations at which a given feature may be present. The location at which a feature can be found may be dependent on one or more of the procedure being performed, the stage of the procedure being performed, a time since a start of the procedure, an action being undertaken, and so on. Tagging features multiple times enables the movement of the features to be better characterised, which can lead to more accurate determinations based on those characterisations. This approach can also help to improve predictor efficiencies, for example by narrowing down the range of likely locations for a feature, or by narrowing down the list of potential features at a given location.

In some examples, the processor is configured to automatically centre a field of view of the displayed representation on a feature. The feature may be predetermined, for example for a given procedure or a given portion of a particular procedure. The feature may be selectable, for example user-selectable. The initiation of the auto-centre (or re-centre) function may be dependent on an auto-centre signal. The auto-centre signal may be generated by a controller, for example by the input device at the controller. In response to receiving the auto-centre signal, the processor may be configured to automatically re-centre the displayed portion of the representation so as to centre the displayed representation on the identified feature. The processor may be configured to re-centre the displayed portion of the representation without causing the imaging device to move. In other words, the imaging device need not move for the field of view of the displayed representation to be centred on a particular feature. For example, the processor may be configured to change the zoom of the displayed representation such that the re-zoomed representation can be centred appropriately without needing the imaging device to move. This approach facilitates a digital re-centring of the feature, which may be quicker than re-centring by moving the imaging device. Further, it enables a re-centring followed by returning to the original viewpoint, in a way which avoids location and/or orientation errors being introduced when returning to the original viewpoint.

Figure 8:
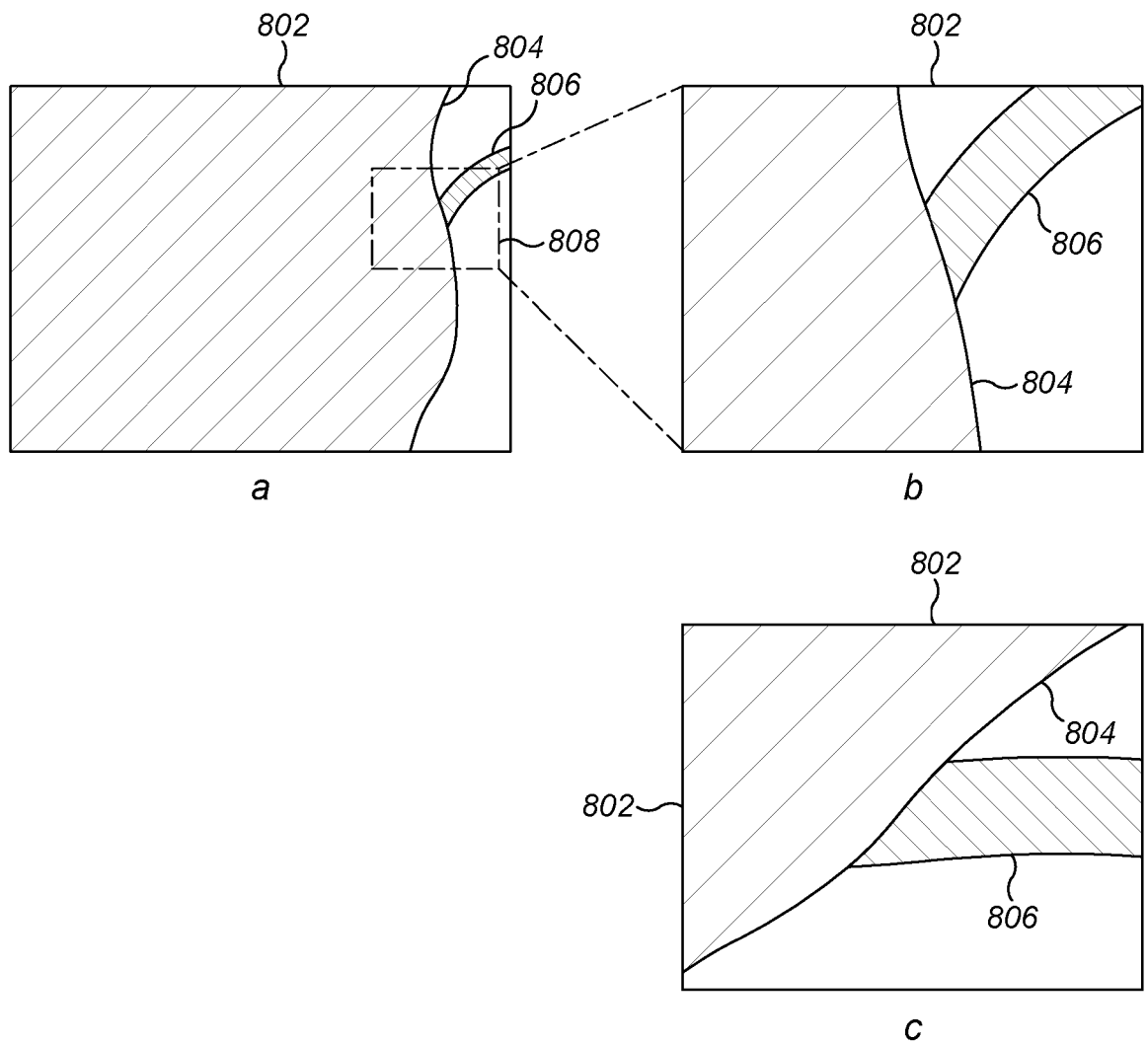
FIG. 8 illustrates examples of displayed portions of a representation.

Such re-centring is illustrated in FIG. 8. FIG. 8*a* shows a display (or a displayed portion of the representation) 802. The displayed portion of the representation comprises (in this highly simplified and schematic example) a feature such as an organ 804 and a blood vessel 806. The junction between the organ 804 and the blood vessel 806 is towards the right-hand side of the displayed portion of the representation 802. This junction may be designated as a feature of interest, and a re-centring signal may be generated in respect of this junction. In response, the processor can zoom the representation so as to centre the zoomed representation on this feature of interest. The zoomed portion of the representation is shown in dashed lines in FIG. 8*a* at 808. FIG. 8*b* shows the re-centred representation, again comprising the organ 804 and the blood vessel 806, but now the junction between the organ 804 and the blood vessel 806 is centrally located in the display 802. Such centring of a feature of interest can enable a more convenient interaction between a user of the system and the system itself. This may be because the centring of the feature of interest allows that feature of interest to be more clearly seen in the displayed portion of the representation.

Figure 9:
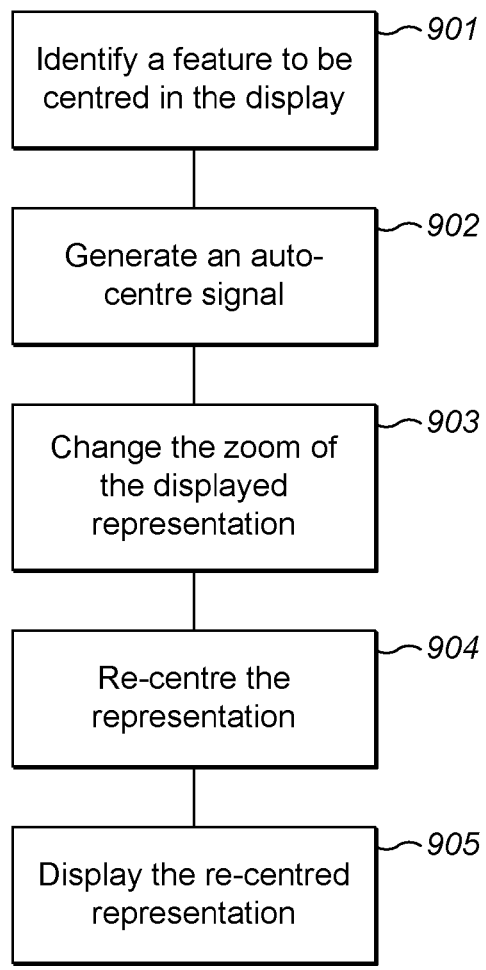
FIG. 9 illustrates a process for centring a portion of a representation.

A process for re-centring the representation is shown in FIG. 9. A feature of interest on which the displayed portion of the representation can be centred is identified (901). The identification of the feature of interest may be performed using one of, or a combination of, the approaches described herein. In some examples the feature of interest may be manually identified and/or labelled. In some examples the feature of interest may be automatically identified and/or labelled. An auto-centre signal can be generated (902). The generation of the auto-centre signal may be automatic, for example in response to one or more criterion being satisfied. The generation of the auto-centre signal may be manual, for example by a user interacting with the input device at the controller. Thus, the initiation of the auto-centring function can be performed in response to input from a user, and/or in response to (for example) a predetermined portion of the procedure being reached, or some other criterion or combination of criteria. The criteria are suitably dependent on user preference and/or the procedure being performed. For example, the criteria may be dependent on a user profile. Thus, the system can be configured so that when a surgeon reaches a predefined point in a procedure at which, for example, it is desirable to obtain a clearer view of a feature of interest, such as where an incision is to be performed, or a stitch to be inserted, an auto-centre signal can be generated.

In response to the auto-centre signal, the processor can be configured to change the zoom of the displayed representation (903). The change in zoom can be dependent on the identified feature. Thus, the zoom can be changed in a way which enables the identified feature to be centred in the zoomed representation. The representation can then be re-centred (904). Suitably the representation is re-centred in dependence on the identified feature. The re-centred representation can be displayed (905). For example, the processor may be configured to output a display signal for causing the display of the representation.

It may also be useful to re-centre an instrument end effector (or a central point between multiple instrument end effectors). The one or more instrument end effectors may be moved into a volume surrounding a feature on the representation, for example a tag. The representation may then be re-centred about that feature (for example by adjusting the zoom of the representation). In some examples, the representation can be re-oriented on the display. An illustration of this can be seen by comparing FIG. 8*b* and FIG. 8*c*. FIG. 8*b* shows an organ 804 and a blood vessel 806. The right-hand edge of the organ 804, as displayed on the display 802, is approximately vertical. The blood vessel 806 extends upwardly to the right. FIG. 8*c* also shows the organ 804 and the blood vessel 806, but in FIG. 8*c* the orientation of the representation has been changed so that the blood vessel extends approximately horizontally. The representation displayed in FIG. 8*c* has been rotated clockwise relative to the representation displayed in FIG. 8*b*. Such a change in orientation of the representation on the display may be useful to enable consistent orientation of a given feature, such as the blood vessel 806. This can provide a user such as a surgeon with a consistent view of a given feature across a number of different procedures, which can enhance the repeatability and/or accuracy of the procedure performed by the surgeon. For example, where the surgeon is to add a stitch, the surgeon may prefer to view the feature being stitched in a horizontal orientation.

The particular orientation to which the representation may be rotated can be selected in dependence on a user input, a user profile, a pre-set orientation and so on. Selecting the orientation in dependence on a user profile can enable each surgeon to view the representation in the orientation that best suits that surgeon.

Re-orienting the representation may be performed by rotating the imaging device and/or by digitally rotating the representation, e.g. at the processor. Re-orienting the representation at the processor has the advantage that the imaging device need not be moved. On re-orienting the representation at the processor, it will typically be appropriate to re-map the controller to the surgical instruments so that the surgeon's movement of the controllers (in, say, a leftwards direction) cause the corresponding surgical instrument to move in the correct direction (in a leftwards direction in the re-oriented frame of reference of the displayed representation of the surgical site). The re-mapping of the controllers to the surgical instruments can be performed in dependence on the displayed representation. Thus, the re-orientation of the representation can be taken into account in the re-mapping.

Health Indicators

As introduced above, pixel data, such as data corresponding to a pixel region of video data captured by an endoscope at a surgical site internal to a patient, can be analysed to derive data that can provide an additional source of feedback to a user of a surgical robotic system. Analysis of endoscope video can be used to identify or characterise movement of an anatomical structure, such as peristaltic movement, and/or tissue perfusion. The analysis suitably permits derivation of one or more parameters related to the anatomical structure and/or tissue perfusion. The derived parameters can be used to provide feedback to a user of the system, enhancing the usability of the system.

Video magnification techniques, such as Eulerian video magnification, take a video sequence as an input. Spatial decomposition may be performed, followed by temporal filtering. The resulting signal may be amplified to derive information. The algorithm used to analyse the video data may be different depending on the information to be derived from the video data. For example, identification of colour changes and deriving a parameter related to the identified colour changes may be performed using a colour change-specific algorithm. In general, 'colour change' can relate to a change in the frequency spectrum—this need not be restricted to visible parts of the spectrum. Identification of movement and deriving a parameter related to the identified movement may be performed using a movement-specific algorithm. Identification of colour changes and movement may be performed together or separately. The video magnification techniques may comprise a tuning stage. The tuning stage may comprise identifying a particular range of values on which to focus. The tuning stage may comprise identifying a particular area on which to focus.

Video data captured by an endoscope can be displayed for viewing by a surgeon or other members of the operating room staff during a procedure. The video data typically shows the surgical site, including patient anatomy, together with images of the end effectors of surgical instruments provided at the surgical site. It is desirable for the surgical robotic system to parameterise at least some aspects of the surgical site.

Such parameterisation of the surgical site, for instance of one or more anatomical structures at the surgical site, can provide additional information to the surgeon. Spatio-temporal changes in the endoscope video, that may not be visible in the displayed video data, can be identified and parameters derived therefrom. Such parameters can be used to enhance or augment a display, such as a display at the surgeon console. Augmentation of the display can provide information to the surgeon that can enable a better user experience.

Thus the present techniques permit enhanced appreciation by a user of the system of small spatio-temporal differences in endoscopic video. For example, the small spatio-temporal differences can be amplified and the amplified differences can be visualised. The nature of the spatio-temporal differences that can be amplified vary depending on the choice of input filter, and can include fine movement of structure, such as anatomical structures, in space and subtle changes in pixel colour amplitude and/or colour or frequency spectrum. The changes in the frequency spectrum need not be visible changes. The changes in the frequency spectrum can include non-visible wavelengths. The term 'colour' can be considered to encompass a range of wavelengths of light, which need not be visible wavelengths, though suitably the range of wavelengths comprises visible wavelengths.

Examples of features of the surgical site that can be identified by analysis of spatio-temporal changes include:
blood flow through and perfusion of at least a portion of patient anatomy or a particular anatomical structure;
the presence of a blood vessel (such as arteries, arterioles and veins); and
movement of anatomical structures, such as peristaltic movement.

The above may be used separately or in combination to identify patient anatomy such as an anatomical structure.

In more detail, analysis of the video data can be used to detect tissue perfusion (and hence blood flow). This can be done during or after a surgical procedure. The analysis can be performed in respect of at least a portion of patient anatomy or a particular anatomical structure in the field of view of the endoscope, such as a particular organ, or another specified region of the field of view. The analysis may be performed for the whole field of view of the endoscope. In general, the analysis may be performed in respect of a pixel region in the video data (which can represent an anatomical structure or a portion thereof, the field of view or a portion thereof, and so on, as will be described in more detail elsewhere). Such analysis of a pixel region in the video data may be performed to determine:
whether anatomy represented by pixels at the pixel region has been devascularised, for example during a procedure to isolate and excise that anatomy;
whether anatomy represented by pixels at the pixel region has an adequate tissue perfusion (and hence blood flow) to enable assessment of potential injury to that anatomy, for example mishandling of that anatomy during the surgical procedure; and
whether anatomy represented by pixels at the pixel region has an adequate tissue perfusion (and hence blood flow) during and after a surgical step or procedure, for the purpose of judging success or likely success of the step or procedure or a likely future outcome following the step or procedure. For example, it is expected to be useful to be able to assess tissue perfusion during and after re-joining of separate bowel ends during a bowel anastomosis (or more generally, a surgical anastomosis), closure of a vaginal cuff, reconstructive plastic surgery, and so on. Assessing the adequacy of tissue perfusion in such situations can enable more accurate monitoring of tissue health and so permit detection of situations that might lead to tissue death or other complications and enable remedial action to be taken before the tissue death or other complications occur. An example of a serious complication is the failure of a bowel anastomosis which can lead to the leakage of faeces into the peritoneal space which can result in life-threatening septic shock. Thus, the ability to detect such a failure is a potentially life-saving feature.

Analysis of the video data can be used to detect and identify blood vessels, such as arteries, arterioles, and veins within the field of view. This can enable augmentation of the representation of the surgical site to identify such detected blood vessels, as described elsewhere herein.

Analysis of the video data can be used to detect peristaltic movements of anatomical structures which may not be otherwise visible. Examples of anatomical structures, the peristaltic movements of which can be detected, include:
  ureters, or a portion thereof; and
  the bowel, or a portion thereof.

Ureters are small retroperitoneal structures that drain urine produced by the kidneys into the bladder. Healthy ureters demonstrate subtle peristaltic movements. These movements can be used to identify the ureters in the endoscope video data. The movements can be used to distinguish the ureters from surrounding tissue. The ability to detect (and amplify) such small peristaltic movements from the video data permits identification of the ureters during a surgical procedure and can therefore help to prevent inadvertent injury to the ureters.

Bowel peristalsis can be used as a surrogate marker of bowel health. Detected bowel peristalsis can provide reassurance that the bowel's blood supply is adequate and that the bowel has not been injured during surgery, e.g. by mispositioning or twisting of the bowel, applying external pressure, having an inadequate blood supply or mishandling by the surgeon. The detection of bowel peristaltic movements enables the movements to be visualised, optionally by amplification of the movements, and measured to generate one or more parameters related to the bowel. The bowel parameters can be used to assess bowel heath during a procedure, at the end of a procedure, and/or after a procedure has been completed. Detecting an absence of peristalsis in the bowel may indicate that a problem exists. Where this is detected during a procedure, or at the end of the procedure, the potential problem can be investigated and remedial action taken before finishing the procedure. The measure of bowel peristalsis, or absence thereof, can be used as a higher-risk predicator of post-operative complications. This can provide a measure useful in determining where monitoring resources should be directed (for example to areas where complications are indicated to be more likely) and/or in determining post-operative actions such as a care pathway.

Figure 12:
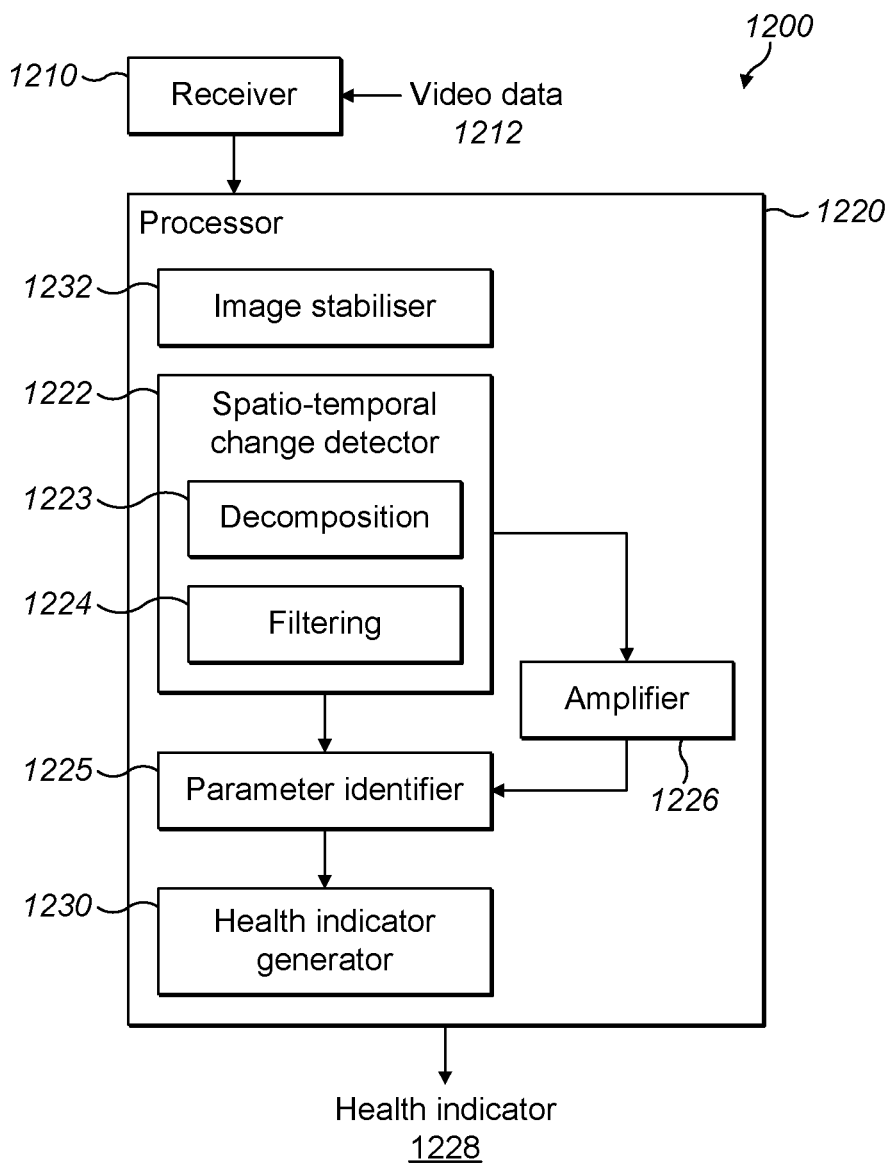
FIG. 12 illustrates an example indicator system.

Reference is made to FIG. 12, illustrating an indicator system 1200 for a surgical robotic system. The indicator system can be for indicating a state of at least a portion of patient anatomy such as an anatomical structure of a patient. The indicator system comprises a receiver 1210 configured to receive video data 1212 of at least a portion of patient anatomy such as an anatomical structure at the surgical site from the endoscope. The indicator system comprises a processor 1220 which is configured to detect a spatio-temporal change in a pixel region of the received video data. The illustrated processor comprises a spatio-temporal change detector 1222 configured to detect the spatio-temporal change. The spatio-temporal change detector may comprise decomposition 1223 and filtering 1224 modules, configured to decompose video data into component parts and to filter the decomposed data. The decomposition and filtering is suitably dependent on the spatio-temporal change to be detected, e.g. an expected spatio-temporal change and/or a spatio-temporal change typical of a particular anatomical structure. The processor is configured to identify, in response to the detected spatio-temporal change, a parameter of the anatomical structure. The illustrated processor comprises a parameter identifier 1224 configured to identify the parameter. The illustrated processor further comprises an amplifier 1226 configured to amplify an output of the spatio-temporal change detector and to pass the amplified output to the parameter identifier. The amplifier need not be provided as a separate module in all examples. The processor is configured to generate a health indicator 1228 indicative of the identified parameter or indicative of a profile of the identified parameter, and to output the generated health indicator. The illustrated processor comprises a health indicator generator 1230 configured to generate the health indicator.

This approach enables the indicator system to provide an indication of the health of an anatomical structure, which might be indicative of the health of the patient. The health indicator can be output so as to indicate the health of the anatomical structure to the surgeon or another member of the surgical team.

The spatio-temporal change may relate to a change in one or both of position of an anatomical feature and colour of an anatomical feature. A positional change may be representative of movement of the anatomical structure or movement of the endoscope relative to the surgical site, or both. Suitably the nature of the movement may be characterised as described elsewhere herein. The movement can be determined to be a movement of at least a portion of an anatomical structure, for example, due to peristalsis. The processor may then identify a parameter characterising the movement. The parameter may relate to one or more of the amplitude of movement, the frequency of movement, the duration of movement, the anatomical structure (or portion thereof) that is moving, and so on. The parameter may comprise a measure of movement. The measure of movement may comprise a rate of movement. The measure of movement may comprise an amplitude and/or orientation of movement.

A colour change may be representative of tissue perfusion, and blood flow. The processor may identify a parameter characterising the colour change. The parameter may relate to one or more of the relative change in colour, the rate of change of colour, the duration of the change of colour, the anatomical structure (or portion thereof) undergoing colour change, and so on. The parameter may relate to the change in one or more colour channel of the video data. The parameter may comprise a measure of blood flow. The measure of blood flow may comprise a measure of heart rate or pulse. The measure of blood flow may comprise a volumetric measurement or estimation of blood flow through or past at least a portion of patient anatomy such as an anatomical structure.

The health indicator may be a binary indicator, such as indicating that an anatomical structure is either healthy or unhealthy. The health indicator can take the form of or comprise a visual signal for display on a display. The health indicator may comprise a visual signal for turning a light on or off. The health indicator can take the form of or comprise an audio signal for driving a speaker. The audio signal may cause the speaker to turn off (or remain off) when the anatomical structure is healthy and to turn on (or remain on) when the anatomical structure is unhealthy. In this way, the audio signal can act as a warning signal. The health indicator can take the form of or comprise a haptic signal for causing generation of haptic feedback via a motor. The haptic signal may cause the motor to turn off (or remain off) when the anatomical structure is healthy and to turn on (or remain on) when the anatomical structure is unhealthy.

The health indicator may comprise a multi-valued indicator. The health indicator may indicate the parameter of an anatomical structure, for example by taking one of a plurality of values corresponding to the parameter. The health indicator may cause display of a coloured indicator, the colour of which is representative of the value of the parameter within a range of parameter values. The health indicator may cause the emission of a sound, the tone and/or volume of which is representative of the value of the parameter within the range of parameter values. The health indicator may cause the display of a representation of an audio waveform. The health indicator may cause audio output of a tone representative of blood flow, for example a periodically varying tone. The health indicator may cause the generation of haptic feedback, the amplitude and/or pattern of which can be representative of the value of the parameter.

The health indicator may comprise a numerical health indicator. For example, where the health indicator comprises a visual signal, the visual signal can cause a display to display a number representative of, for example, a heart rate and/or a respiratory rate of a patient derived from the video data.

The processor is suitably configured to store the parameter values to generate a profile of the parameter value over time. The health indicator may be indicative of the profile of the parameter. For example, where the parameter is a measure of a patient's heart rate, the profile of the parameter can comprise a graph of the heart rate over time.

The processor can compare the identified parameter with a reference parameter of the patient anatomy or anatomical structure. The processor can generate the health indicator in dependence on a result of the comparison. The reference parameter is suitably a value of the parameter that characterises whether or not the patient anatomy, anatomical structure or the patient is healthy. For example, where the parameter is a heart rate, and it is known that heart rates in excess of X beats per minute or lower than Y beats per minute are indicative of poor health, the processor can determine whether the heart rate identified from the video data is between X and Y beats per minute. If within this range, the processor can generate the health indicator to indicate that the parameter is in a healthy range. If outside this range the processor can generate the health indicator to indicate that the parameter is outside a healthy range. Suitably, the values of X and Y can be selected in dependence on the procedure being performed, the stage in the procedure, patient history and/or physiology and so on. The values of X and Y are suitably dynamically variable. In general, the reference parameter with which the identified parameter is compared may be determined in dependence on one or more of the procedure being performed, the stage in the procedure, an anatomical structure identified in the video data, patient history and/or physiology, and so on.

The processor is suitably configured to determine whether the identified parameter is within a predefined range of the reference parameter, and the health indicator can comprise a warning where the identified parameter is outside the predefined range. Taking the example of the heart rate above, the health indicator can indicate that the heart rate is in an unhealthy range when it drops below Y beats per minute. However, if the heart rate drops a predefined further amount, say 10 beats per minute less than Y, the indicator system can be configured to generate a health indicator comprising a warning. Such a warning can usefully indicate where the value of the identified parameter reaches critical levels. This can enable remedial action to be taken at an appropriate time.

The spatio-temporal change suitably comprises one or more of a positional change of at least a portion of the patient anatomy or anatomical structure in the pixel region; an intensity change of at least a portion of the patient anatomy or anatomical structure in the pixel region; and a colour change of at least a portion of the patient anatomy or anatomical structure in the pixel region. The change may be a change with respect to at least one pixel of the pixel region.

Suitably the processor is configured to identify a relative movement between the endoscope and a bulk of the anatomical structure and/or between the bulk of the anatomical structure and a remainder of the surgical site and to detect the spatio-temporal change in dependence on the identified relative movement. In this way, the indicator system can take account of movement that is not indicative of anatomical peristaltic movements, or other movements that it may be desirable to detect, and can filter these movements out so as more accurately to detect the desired movements. The desired movements may be smaller than the movements to be filtered out. For example, where a portion of the bowel is visible in the video data and the endoscope is moving through the surgical site, it is likely that the bowel peristaltic movements will be much smaller than the overall movement of the bowel within the field of view of the endoscope.

Suitably therefore, the processor is configured to identify a relative movement between the surgical site and the endoscope. This may be performed by detecting movement of a bulk of the surgical site in the field of view. For example, where at least a predefined proportion of the surgical site moves in a given direction, it can be determined that the endoscope is moving relative to the surgical site. That overall movement can be quantified, and filtered out before analysing for movement in the pixel region. Relative movement between the surgical site and the endoscope may be determined from kinematic data of the robotic system. Thus, suitably the processor is configured to access the kinematic data and to determine from that kinematic data a measure of movement between the surgical site and the endoscope. The determined measure of movement can be filtered out before analysing for movement in the pixel region.

In a similar manner, movement of a portion of the surgical site can be taken into account. For example, a kidney may move at the surgical site, for example by being moved by a surgeon. The movement of the whole kidney can be detected and filtered out before analysing the video data for movements of portions of the kidney, or structures extending therefrom, such as ureters.

A movement of interest may be identified in the video data by using a filter such as a frequency filter. For example, a peristaltic movement can be expected to occur with a characteristic frequency or with a frequency within a characteristic frequency range. A bulk movement of an anatomical structure may occur with a frequency outside such a range. Thus, the video data can be filtered to enable analysis only within the frequency range of interest.

The pixel region may move between frames of the video data. The anatomical structure may move relative to the endoscope. This movement can be caused by the endoscope moving relative to the surgical site, and/or by the anatomical structure moving relative to the surgical site. Suitably the pixel region relates to a given anatomical structure or portion thereof. Thus, as the anatomical structure moves in the field of view, the pixel region moves in a corresponding manner. That is, the movement of the anatomical structure can be tracked, and the tracking used to adjust the location in the video data of the pixel region. Thus the processor can be configured to detect the spatio-temporal change in dependence on pixels in frames of the video data that correspond to the same portion of the anatomical structure.

The processor may be configured to use image stabilisation techniques to stabilise the video data captured by the endoscope. Use of such image stabilisation techniques can help to filter out undesired movements in the video data. This can improve the accuracy with which the parameter can be identified. The processor may comprise an image stabiliser 1232 configured to stabilise the received video data.

The pixel region may form a portion of, or all of, the field of view of the endoscope. The pixel region may comprise a region of interest within the field of vision. The region of interest may be defined by one or more of:
- a bounding box on the display, which may be central to the display or offset from the centre in a desired direction by a desired amount. The offset direction and/or distance may be pre-set. The offset direction and/or distance may be user-definable.
- a moveable and/or resizable bounding box on the display.
- an abstract region as drawn by the operator, for example by manipulating the input device.
- a single point of focus or multiple points of focus.
- an anatomical structure or other feature, which may be determined automatically (for example by video processing such as image matching, image recognition, and so on). The anatomical structure or other feature may be tracked across frames of the video data.
- a zone of fixed or variable size around one or more instrument tips. The size of the zone may be selectable by a user. The size of the zone may be selected in dependence on the procedure being carried out, the stage of the procedure, surgeon preference, and so on.

The bounding box may be a polygonal bounding box.

The pixel region can be selectable, for example user selectable. The pixel region can be selected in response to a user signal. The processor is suitably configured to receive the user signal and to select the pixel region is response to the received user signal. The user signal can be output by a controller having an input device. The controller is suitably configured to output the user signal in response to user input relating to the video data captured by the endoscope.

The pixel region may be selected automatically, for example in dependence on an anatomical structure identifying signal. The anatomical structure identifying signal may be generated from image analysis of the video data, for example using image recognition techniques to identify an anatomical structure within the field of view of the endoscope. The anatomical structure identifying signal may be generated in dependence on information pertaining to the surgical site available to the system. For example, where a model of the surgical site exists and can be compared to data indicating the position and orientation of the endoscope, which might be derived from kinematics data for example, it can be possible to identify an expected anatomical structure within the field of view of the endoscope.

Suitably the processor is configured to amplify the spatio-temporal change and to generate the health indicator using the amplified spatio-temporal change. The spatio-temporal change may be amplified by the amplifier 1226. The spatio-temporal change can comprise a change between a first value and a second value. The processor can amplify the spatio-temporal change by multiplying the first value with a first amplification factor and by multiplying the second value by a second amplification factor. In some cases, only one of the first value and the second value is multiplied by its respective multiplication factor. This can be achieved by setting the other multiplication factor to 1.

The spatio-temporal change can be amplified about a mid-point of the range between the first value and the second value. The spatio-temporal change can be amplified symmetrically about a mid-point of the range between the first value and the second value. The first amplification factor and the second amplification factor may be the same, though they need not be. The spatio-temporal change can be amplified about a selected value between the first value and the second value. The selected point need not be half-way between the first value and the second value.

One or both of the first amplification factor and the second amplification factor can be selected in dependence on one or more of:
- a number of detected spatio-temporal changes in the pixel region; This can reduce the chances of the amplified spatio-temporal change obscuring another change, including another detected spatio-temporal change. Where a plurality of spatio-temporal changes are detected, the amplification factors can be selected appropriately. This can include selecting smaller amplification factors. This can include selecting amplification factors that skew the amplified change away from another detected spatio-temporal change.
- a surgeon preference;
- a procedure being carried out using the surgical robotic system or a stage of the procedure;
- the patient anatomy or anatomical structure;
- the identified parameter; and
- the comparison of the identified parameter with the reference parameter.

For example, where the health indicator indicates that the anatomical structure is in poor health, the amplification can be increased. Where the health indicator comprises a warning, the amplification can be increased. Suitably, the amplification is increased further in the event of the health indicator comprising the warning.

Figure 13:
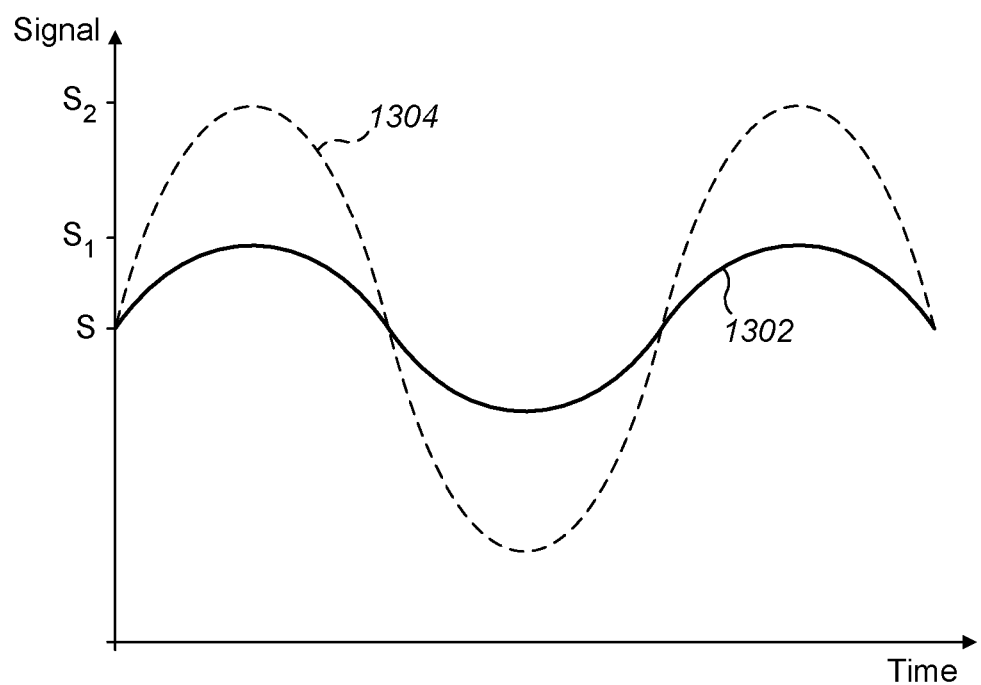
FIG. 13 schematically illustrates an example of amplification of a parameter.

A schematic example of amplification of a parameter is illustrated in FIG. 13. FIG. 13 shows a time varying value of an identified parameter 1302. The identified parameter as illustrated varies symmetrically about a value s, having a maximum amplitude of $s_1$. The amplified parameter varies symmetrically about s but with a greater maximum amplitude of $s_2$. Where the identified parameter is a position, the amplified position can make it easier to appreciate the change, for example visually.

As discussed, the indicator system can generate a health indicator indicative of a parameter of an anatomical structure, such as a heart rate or a respiratory rate of a patient. It is known to determine heart rates and respiratory rates in other ways, for example using standard operating theatre equipment. Suitably the indicator system is configured to have access to a further parameter. The further parameter can comprise a heart rate and/or respiratory rate measured using such standard equipment. The further parameter can be received by the indicator system. The further parameter can be received by the surgical robotic system. The further parameter is suitably received from a monitoring system remote from the surgical robotic system. The further parameter can be used to calibrate the identified parameter. This can enhance the accuracy of the indicator system.

The receiver is suitably configured to receive further video data of an external portion of the patient. The further video data can comprise video of an exposed surgical site and/or of the skin of a patient. Suitably the processor is configured to detect a further spatio-temporal change in a pixel region of the received further video data. The processor can identify the further parameter in response to the detected further spatio-temporal change.

The generated health indicator can comprise a visual indicator. The processor can output the generated health indicator for display on a display. The generated health indicator can comprise an audio indicator. The processor can output the generated health indicator for driving a speaker. The generated health indicator can be output for overlay on at least a portion of a display, such as a display for displaying the representation of the surgical site. The overlay may be partially transparent. The overlap may replace the portion of the representation of the surgical site on which it is overlaid. Thus, the health indicator may comprise a modified portion of video which can be overlaid on the representation of the surgical site.

Figure 14:
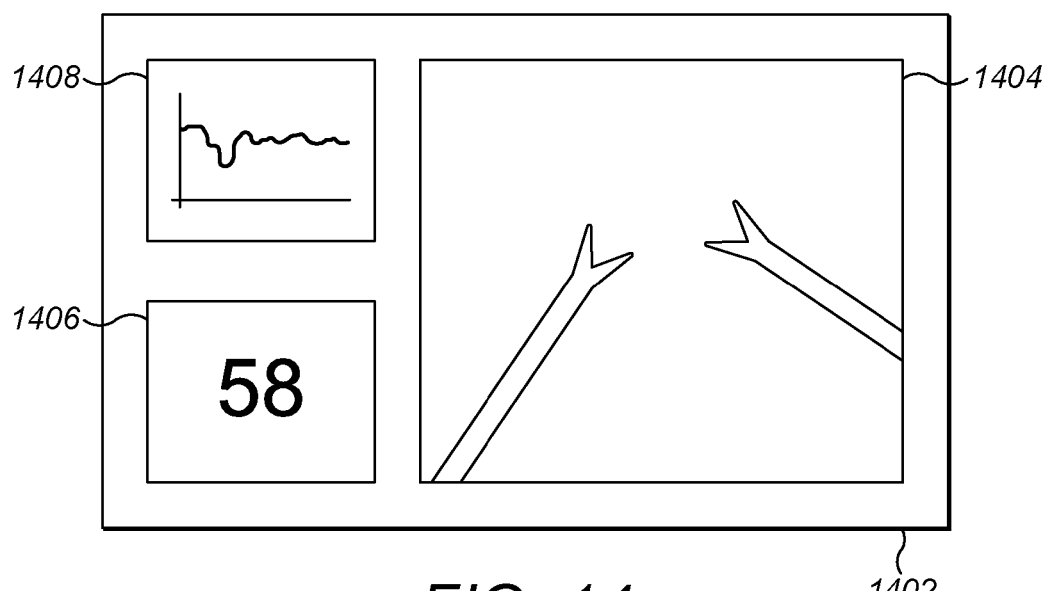
FIG. 14 schematically illustrates an example of the display of health indicators.

A schematic example of the display of health indicators is illustrated in FIG. 14. FIG. 14 shows a display 1402. The display comprises a representation of the surgical site, including two end effectors 1404. The display also comprises two health indicators. A first health indicator 1406 comprises a numerical value of an identified parameter such as a heart rate. A second health indicator 1408 comprises a profile of an identified parameter. The second health indicator may comprise a profile of the identified parameter shown in the first health indicator, though this need not be the case. Any two or more health indicators may be displayed on the display. The selection of the health indicator, or the health indicators, for display can be made in dependence on one or more of the procedure being performed, a stage in the procedure being performed, surgeon preference, a value of the identified parameter or values of the identified parameters, and so on.

Figure 15:
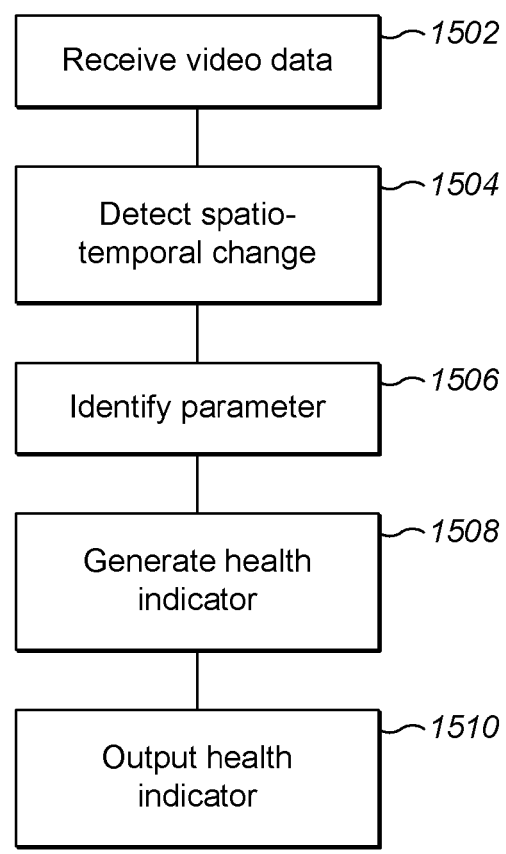
FIG. 15 illustrates an example method of indicating a state of an anatomical structure of a patient.

A method of indicating a state of at least a portion of patient anatomy such as an anatomical structure of a patient will now be described with reference to FIG. 15. Video data is received at 1502. The video data is received from an endoscope at a surgical site internal to a body cavity of a patient. The video data comprises video data of an anatomical structure at the surgical site. At 1504 a spatio-temporal change in a pixel region of the received video data is detected. In response to the detected spatio-temporal change, at 1506 a parameter of the anatomical structure is identified. A health indicator indicative of the identified parameter or indicative of a profile of the identified parameter is then generated, at 1508. At 1510 the generated health indicator is output.

Operating Modes

The spatio-temporal change can be detected by using a spatio-temporal difference algorithm. The spatio-temporal difference algorithm may be enabled and disabled multiple times during a procedure. The indicator system may be operable in one of several modes of operation. Suitably the modes of operation comprise:

a perfusion mode
The perfusion mode may be used to amplify small changes in the video corresponding to blood flow. For example, in the perfusion mode the indicator system can detect small changes in the red colour channel of the video data. Thus in the perfusion mode the indicator system is suitably able to determine the presence or absence of perfusion. The indicator system can, in this mode, be calibrated with a filter to detect perfusion for a range of human heart rates. Thus suitably, the indicator system is configured to perform time analysis of the video data, for example the red channel of the video data, to identify a heart rate. The indicator system can, in the perfusion mode, apply a red and/or infrared spectrum filter so as to detect the presence of oxygenated and deoxygenated haemoglobin.

a peristalsis mode
The peristalsis mode may be used to amplify small movements in the video. The indicator system can, in the peristalsis mode, detect typical movements of interest, including colonic peristaltic and ureteric peristatic movements. The indicator system can detect such peristaltic movements by identifying movements with an amplitude of movement and/or a frequency of movement that are characteristic of the movement of interest, e.g. of colonic peristatic movements or of ureteric peristaltic movements.

a vessel mode
The vessel mode may be used to amplify small movements due to pulsatile blood flow. The indicator system can, in the vessel mode, detect movements at a frequency of interest or in a frequency range of interest. This can permit the indicator system to identify blood vessels. The indicator system can, in the vessel mode, apply a red and/or infrared spectrum filter so as to detect the presence of oxygenated and deoxygenated haemoglobin.

a mixed mode
The mixed mode is a hybrid mode that comprises analysis from any two or more of the other modes.

Outputting the Health Indicator

The health indicator is output in one of several different ways. As discussed elsewhere herein, the health indicator can comprise a visual signal and/or an audio signal. The health indicator can be output to a user of the surgical robotic system to identify the detected spatio-temporal change in different ways.

The spatio-temporal change can be amplified and the health indicator can comprise the amplified spatio-temporal change. The health indicator can comprise the amplified spatio-temporal change added to the video data. The amplified spatio-temporal change can amplify the colour and/or movement in the video data. Thus, these changes can become more visually apparent to a user of the system.

The heath indicator can comprise a coloured region for recolouring a portion of the display. For example, the coloured region can be partially transparent to enable a colour map to be overlaid on a portion of the display such as a portion of the display displaying the representation of the surgical site. The recoloured portion can be used to highlight an area of interest in the representation of the surgical site. The recoloured portion can be used to highlight an area in which a spatio-temporal change has been detected. For example, the recoloured portion can indicate an area in the field of view in which a peristaltic movement has been detected.

The health indicator can comprise an audio signal indicating the presence or otherwise of a spatio-temporal change, or a spatio-temporal change of interest (e.g. one which meets predefined criteria). The health indicator can indicate the presence or otherwise of a spatio-temporal change of interest at a particular pixel region in the field of view, for example a pixel region surrounding an end effector tip. Thus, the end effector may be moved through the field of view of the endoscope and the health indicator can indicate whether the end effector passes over a region in which there is a spatio-temporal change of interest. This arrangement permits a user of the indicator system to move an end effector across anatomical structures visible in the video data and to assess whether or not a spatio-temporal change is present in respect of each anatomical structure.

The audio signal can be rescaled, for example by being frequency adjusted. Such a rescaled audio signal can be used to quantify colour change and/or movement. The quantified colour change and/or movement may be quantified relative to a background colour change or a background movement, respectively. The quantified colour change and/or movement may be quantified relative to a predefined colour change or predefined movement, respectively.

The detected spatio-temporal change may, in general, be a change relative to a defined value or a defined baseline value for a given parameter. The baseline can be taken relative to the frame of the video data as a whole, or a subregion of the frame. The baseline can be taken relative to a previous frame or a subregion of the previous frame. The previous frame may be an immediately preceding frame, or an earlier frame. The previous frame may be selected during a calibration phase. The baseline may be an average value over the relevant region, such as the mean value over that region.

As discussed elsewhere herein, the indicator system can output an indication of a patient's heart rate and/or respiratory rate, derived from video data captured by the endoscope. This heart rate/respiratory rate can be correlated with output from a patient's vital signs monitor. The result of the correlation can be used to provide confirmation of an adequate signal detection. For example, the correlation can confirm that a measured tissue perfusion at a bowel anastomosis is a true signal which is representative of the patient's actual heart rate. Such correlation can be used to determine when a detected heart rate or respiratory rate is not a true heart rate or respiratory rate. This can result in more accurate data being determined at the indicator system.

The health indicator can comprise a measure of a parameter globally (e.g. the whole of the field of view of the endoscope, or within a body cavity (for example by aggregating the measure over a plurality of frames of the video data), or within a defined zone of the field of view or body cavity (e.g. a zone defined in software, for example by a user during a planning phase), or for a particular anatomical structure. A measure of perfusion can be provided as an absolute measure or as a relative measure. The relative measure may be provided relative to another anatomical structure, relative to the field of view, relative to a remainder of the field of view (i.e. not including the anatomical structure being measured), relative to the pixel region or another region at a specified point in time or over a specified time range, or relative to a predefined value.

The indicator system may be configured to identify the parameter at a specified point in time or over a specified time range. The specified time range may, for example, be the duration of a surgical procedure or the duration of a stage of the surgical procedure.

The indicator system may be useful in detecting subclinical or subtle patient seizure activity, for example in neurosurgery. The indicator system may be useful in detecting subtle muscle movements, for example of facial muscles, that may be related to a light plane or depth of anaesthesia. Thus the indicator system may be configured to monitor a depth of anaesthesia of a patient during a surgical procedure. A measure of the depth of anaesthesia can be correlated with other vital signs monitored through the indicator system and/or remotely from the indicator system. The correlation can provide additional information to a surgeon to enable them to more effectively monitor the health of a patient undergoing a surgical procedure.

The indicator system is suitably configured to interface with a data system. The indicator system can be configured to output the health indicator to the data system. This can enable automatic reporting of perfusion detection or of a measured perfusion index. The data system can comprise an electronic patient record system. The indicator system is suitably configured to interface with the data system over a network. The network may comprise a wired network. The network may comprise a wireless network. Suitably the network is a private network such as a hospital network.

The indicator system may be configured to generate a patient risk score. The health indicator may comprise the patient risk score. The data system may be configured to generate the patient risk score based on data output from the indicator system. The patient risk score is a measure of risk to a patient and can be dependent on the procedure. The patient risk score is suitably determined in dependence on the identified parameter values. For example, the patient risk score can give a measure of the risk of failure of a bowel anastomosis given a measure of tissue perfusion as determined by the indicator system. The patient risk score can be determined based on additional surgical data, patient data and/or surgeon data, any or all of which may be determined by the indicator system, by the surgical robotic system, or from predetermined data.

The techniques described herein could be used for non-surgical robotic purposes. For example, they could be used in robotic systems, or systems more generally, in which it is desirable to obtain additional information in relation to a procedure such as a robotic procedure.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. An indicator system for a surgical robotic system for indicating a state of at least a portion of patient anatomy, the surgical robotic system comprising a robot having a base and an arm extending from the base, the arm holding an endoscope at an end of the arm distal from the base, the endoscope being configured for insertion into a body cavity of the patient for observing a surgical site internal to a body of the patient, the indicator system comprising:
    a receiver configured to receive video data of at least a portion of patient anatomy at the surgical site from the endoscope; and
    a processor configured to:
        detect a spatio-temporal change in a pixel region of the received video data;

identify, in response to the detected spatio-temporal change, a parameter of the patient anatomy;
generate a health indicator indicative of the identified parameter or indicative of a profile of the identified parameter; and
output the generated health indicator;
the processor being further configured to:
identify a relative movement between the endoscope and a bulk of the patient anatomy and/or between the bulk of the patient anatomy and a remainder of the surgical site and to detect the spatio-temporal change in dependence on the identified relative movement.

2. An indicator system according to claim 1, in which the processor is configured to compare the identified parameter with a reference parameter of the patient anatomy, and to generate the health indicator in dependence on a result of the comparison.

3. An indicator system according to claim 1, in which the spatio-temporal change comprises one or more of:
a positional change of at least a portion of the patient anatomy in the pixel region;
an intensity change of at least a portion of the patient anatomy in the pixel region; and
a change in the frequency spectrum of at least a portion of the patient anatomy in the pixel region.

4. An indicator system according to claim 1, in which the processor is configured to amplify the spatio-temporal change and to generate the health indicator using the amplified spatio-temporal change.

5. An indicator system according to claim 4, in which, where the spatio-temporal change comprises a change between a first value and a second value, the processor is configured to amplify the spatio-temporal change by multiplying the first value with a first amplification factor and by multiplying the second value by a second amplification factor.

6. An indicator system according to claim 4, in which one or both of the first amplification factor and the second amplification factor is selected in dependence on one or more of:
a number of detected spatio-temporal changes in the pixel region;
a surgeon preference;
a procedure being carried out using the surgical robotic system or a stage of the procedure;
the patient anatomy;
the identified parameter; and
the comparison of the identified parameter with the reference parameter.

7. An indicator system according to claim 1, in which the processor is configured to select the pixel region in response to one or more of a received user selection signal and an anatomical structure identifying signal.

8. An indicator system according to claim 7, in which the processor is configured to identify, in the received video data, one or more anatomical structure and to output the anatomical structure identifying signal in response to identifying the one or more anatomical structure.

9. An indicator system according to claim 1, in which the spatio-temporal change comprises a peristaltic movement of at least a portion of an anatomical structure.

10. An indicator system according to claim 1, in which the pixel region comprises one or more of:
a representation of at least a portion of a ureter, and the spatio-temporal change comprises a peristaltic movement of the ureter; and
a representation of at least a portion of a bowel, and the spatio-temporal change comprises a peristaltic movement of the bowel.

11. An indicator system according to claim 1, in which the processor is configured to calibrate the identified parameter using a further parameter.

12. An indicator system according to claim 11, in which the parameter and further parameter relate to one or both of a patient heart rate and a patient respiratory rate.

13. An indicator system according to claim 11, in which the receiver is configured to receive further video data of an external portion of the patient and the processor is configured to:
detect a further spatio-temporal change in a pixel region of the received further video data; and
identify the further parameter in response to the detected further spatio-temporal change.

14. An indicator system according to claim 1, in which the generated health indicator comprises one or more of:
a visual indicator and the processor is configured to output the generated health indicator for display on a display;
an audio indicator and the processor is configured to output the generated health indicator for driving a speaker; and
a haptic indicator and the processor is configured to output the generated health indicator for driving a motor for providing haptic feedback.

15. A non-transitory computer readable storage medium having stored thereon computer readable instructions that, when executed at a computer system, cause the computer system to perform a method comprising:
receiving, from an endoscope at a surgical site internal to a body cavity of a patient, video data of an anatomical structure at the surgical site;
detecting a spatio-temporal change in a pixel region of the received video data;
identifying, in response to the detected spatio-temporal change, a parameter of the anatomical structure;
generating a health indicator indicative of the identified parameter or indicative of a profile of the identified parameter;
displaying part or all of a representation of at least a portion of the surgical site;
controlling an indicator on the display;
receiving user input relating to the representation and outputting an augmentation signal in response to the received user input; and
augmenting the representation of the surgical site in response to the augmentation signal and the generated health indicator.

16. A method for augmenting a representation of a surgical site at which a surgical procedure can be carried out, comprising:
receiving, from an endoscope at a surgical site internal to a body cavity of a patient, video data of an anatomical structure at the surgical site;
detecting a spatio-temporal change in a pixel region of the received video data;
identifying, in response to the detected spatio-temporal change, a parameter of the anatomical structure;
generating a health indicator indicative of the identified parameter or indicative of a profile of the identified parameter;

displaying part or all of a representation of at least a portion of the surgical site;

controlling an indicator on the display;

receiving user input relating to the representation and outputting an augmentation signal in response to the received user input; and augmenting the representation of the surgical site in response to the augmentation signal and the generated health indicator.

17. A method according to claim 16, comprising at least one of:

generating the representation of the surgical site in dependence on a stored representation of the surgical site; and generating the representation of the surgical site in dependence on the received video data.

18. A method according to claim 16, in which the indicator comprises a portion of an imaged end effector of the surgical robotic system, and the method comprises controlling the indicator on the display by controlling the end effector.

19. A method according to claim 16, comprising, where the representation of the surgical site comprises a plurality of augmentations, determining at least one of:

a number of augmentations;

a distance between the plurality of augmentations;

an area enclosed by the plurality of augmentations; and a volume enclosed by the plurality of augmentations.

20. A method according to claim 16, comprising displaying, on at least one of the display and an auxiliary display, one or more of:

a number of augmentations;

a line connecting a plurality of augmentations;

an area enclosed by a plurality of augmentations; and a volume enclosed by a plurality of augmentations.

\* \* \* \* \*